(12) United States Patent
Zheng et al.

(10) Patent No.: US 7,037,669 B2
(45) Date of Patent: May 2, 2006

(54) ASSAYS FOR AMPHETAMINE AND METHAMPHETAMINE USING STEREOSPECIFIC REAGENTS

(75) Inventors: Yi Feng Zheng, Wilmington, DE (US); Khaled A. Yamout, Carlsbad, CA (US); Donald E. Berger, Jr., San Jose, CA (US); Mae W. Hu, Los Altos Hills, CA (US); Hshiou-ting Liu, Milpitas, CA (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 10/805,813

(22) Filed: Mar. 22, 2004

(65) Prior Publication Data
US 2005/0208603 A1 Sep. 22, 2005

(51) Int. Cl.
*G01N 33/53* (2006.01)
*G01N 33/531* (2006.01)
*C07K 16/00* (2006.01)
*C07K 17/02* (2006.01)
*C07D 317/58* (2006.01)

(52) U.S. Cl. .............. 435/7.9; 435/961; 435/975; 435/7.1; 435/188; 436/544; 436/546; 530/388.9; 530/389.8; 530/402; 530/403; 530/405; 424/175.1; 549/444; 549/443; 548/526; 564/336

(58) Field of Classification Search ............ 435/961, 435/975, 7.1, 7.9, 188; 530/388.9, 389.8, 530/403, 405, 402; 436/546, 544; 564/336; 424/175.1; 549/443, 444; 548/526
See application file for complete search history.

(56) References Cited

U.S. PATENT DOCUMENTS

| | | | |
|---|---|---|---|
| 1,879,003 A | 9/1932 | Alles | 564/381 |
| 1,921,424 A | 8/1933 | Nabenhauer | 167/58 |
| 2,344,356 A | 3/1944 | Hildebrandt | 260/570.8 |
| 3,117,160 A | 1/1964 | Holland | 260/570.8 |
| 3,547,999 A | 12/1970 | Shulgin | 260/570.8 |
| 3,709,868 A | 1/1973 | Spector | 260/121 |
| 3,758,691 A | 9/1973 | Carlsson et al. | 424/330 |
| 3,763,218 A | 10/1973 | Kaiser et al. | 260/471 A |
| 3,766,162 A | 10/1973 | Spector | 260/112 R |
| 3,775,536 A | 11/1973 | Spector et al. | 424/1 |
| 3,847,950 A | 11/1974 | Suh et al. | 260/340.5 |
| 3,867,366 A | 2/1975 | Rubenstein et al. | 260/121 |
| 3,875,011 A | 4/1975 | Rubenstein et al. | 195/99 |
| 3,911,016 A | 10/1975 | Klingler et al. | 260/570.8 R |
| 3,995,021 A | 11/1976 | Gross | 424/1.5 |
| 3,996,344 A | 12/1976 | Gross | 424/1.5 |
| 4,016,146 A | 4/1977 | Soares | 260/112 R |
| 4,022,878 A | 5/1977 | Gross | 424/1.5 |
| 4,036,823 A | 7/1977 | Soares | 260/112 R |
| 4,041,076 A | 8/1977 | Avenia et al. | 260/559 A |
| 4,058,642 A | 11/1977 | Renth et al. | 424/330 |
| 4,064,228 A | 12/1977 | Gross | 424/1 |
| 4,073,798 A | 2/1978 | Suh | 260/340.5 R |
| 4,097,586 A | 6/1978 | Gross | 424/1 |
| 4,129,598 A | 12/1978 | Giudicelli et al. | 260/570.8 R |
| 4,218,539 A | 8/1980 | Weltman | 435/188 |
| 4,220,565 A | 9/1980 | Katz | 260/6 |
| 4,329,281 A | 5/1982 | Christenson et al. | 260/112 B |
| 4,595,656 A | 6/1986 | Allen et al. | 435/7 |
| 4,680,338 A | 7/1987 | Sundoro | 525/54.1 |
| 4,686,181 A | 8/1987 | Dona | 435/7 |
| 4,760,142 A | 7/1988 | Primes et al. | 544/287 |
| 4,843,147 A | 6/1989 | Levy et al. | 530/391 |
| 4,847,195 A | 7/1989 | Khanna et al. | 435/7 |
| 4,868,132 A | 9/1989 | Byrnes et al. | 436/546 |
| 4,952,336 A | 8/1990 | Brynes et al. | 252/301.16 |
| 4,990,443 A | 2/1991 | Huber et al. | 435/7.9 |
| 5,026,827 A | 6/1991 | Miyazaki et al. | 530/405 |
| 5,101,015 A | 3/1992 | Brynes et al. | 530/363 |
| 5,135,863 A | 8/1992 | Hu et al. | 435/188 |
| 5,145,791 A | 9/1992 | Zeitvogel et al. | 436/546 |
| 5,198,587 A | 3/1993 | Imai et al. | 564/374 |
| 5,227,472 A | 7/1993 | Yoshioka | 530/403 |
| 5,233,025 A | 8/1993 | Miyazaki et al. | 530/388.9 |
| 5,256,409 A | 10/1993 | Blincko | 424/85.8 |
| 5,262,333 A | 11/1993 | Heiman et al. | 436/537 |
| 5,266,720 A | 11/1993 | Gallacher et al. | 560/60 |
| 5,270,166 A | 12/1993 | Parsons et al. | 435/7.4 |
| 5,294,638 A | 3/1994 | Hell et al. | 514/452 |
| 5,328,828 A | 7/1994 | Hu et al. | 435/7.9 |
| 5,336,621 A | 8/1994 | Primes et al. | 436/534 |
| 5,354,693 A | 10/1994 | Byrnes et al. | 436/537 |
| 5,372,949 A | 12/1994 | Zeitvogel et al. | 436/546 |
| 5,373,092 A | 12/1994 | Gallacher et al. | 435/7.93 |
| 5,424,204 A | 6/1995 | Aoyama et al. | 435/188 |
| 5,470,997 A | 11/1995 | Buechler et al. | 558/254 |
| 5,492,841 A | 2/1996 | Craig | 436/534 |
| 5,501,987 A | 3/1996 | Ordonez et al. | 436/534 |

(Continued)

FOREIGN PATENT DOCUMENTS

DE    2844427    4/1980

(Continued)

*Primary Examiner*—Long V. Le
*Assistant Examiner*—Shafiqul Haq
(74) *Attorney, Agent, or Firm*—Theodore J. Leitereg

(57) ABSTRACT

Methods, compositions and kits are disclosed. Enzyme conjugates of Formula I may be employed in assays for the determination of an amphetamine and/or a methamphetamine. Immunogenic conjugates of Formula I may be employed to prepare antibodies for an amphetamine and/or for a methamphetamine for use in assays for the determination of an amphetamine and/or a methamphetamine. The enzyme conjugates may also be employed to screen antibodies for use in such methods.

59 Claims, 2 Drawing Sheets

U.S. PATENT DOCUMENTS

| | | | |
|---|---|---|---|
| 5,514,559 A | 5/1996 | Markert-Hahn et al. | 435/7.92 |
| 5,518,887 A | 5/1996 | Parsons et al. | 435/7.1 |
| 5,525,524 A | 6/1996 | Buechler et al. | 436/518 |
| 5,610,283 A | 3/1997 | Buechler | 530/404 |
| 5,616,503 A | 4/1997 | Self | 436/518 |
| 5,643,732 A | 7/1997 | Strahilevitz | 435/7.1 |
| 5,840,588 A | 11/1998 | Strahilevitz | 436/518 |
| 5,851,776 A | 12/1998 | Valkirs | 435/7.1 |
| 5,976,812 A | 11/1999 | Huber et al. | 435/7.1 |
| 6,033,890 A | 3/2000 | Jakobovits et al. | 435/190 |
| 6,090,567 A | 7/2000 | Jakobovits et al. | 435/7.9 |
| 6,140,137 A | 10/2000 | Sigler et al. | 436/536 |
| 6,214,859 B1 | 4/2001 | Yoneda et al. | 514/419 |
| 2002/0090661 A1* | 7/2002 | Wang et al. | 435/7.92 |
| 2003/0170917 A1 | 9/2003 | Hui et al. | 436/547 |
| 2003/0175995 A1* | 9/2003 | Hui | 436/547 |

FOREIGN PATENT DOCUMENTS

| | | | |
|---|---|---|---|
| EP | 828880 | 7/1958 | |
| EP | 1467560 | 11/1975 | 317/58 |
| EP | 0 183901 A2 | 11/1985 | 33/531 |
| EP | WO 86/05189 | 9/1986 | 33/531 |
| EP | 0 517325 B2 | 6/1992 | 33/532 |
| EP | 1 321772 A1 | 12/2002 | 33/94 |
| JP | 53066417 A | 6/1978 | 436/534 |
| JP | 56125666 A | 10/1981 | 436/537 |
| JP | 63220932 | 9/1988 | 530/388.9 |
| JP | 2069196 A | 3/1990 | |
| WO | WO 90/15798 | 12/1990 | |

\* cited by examiner

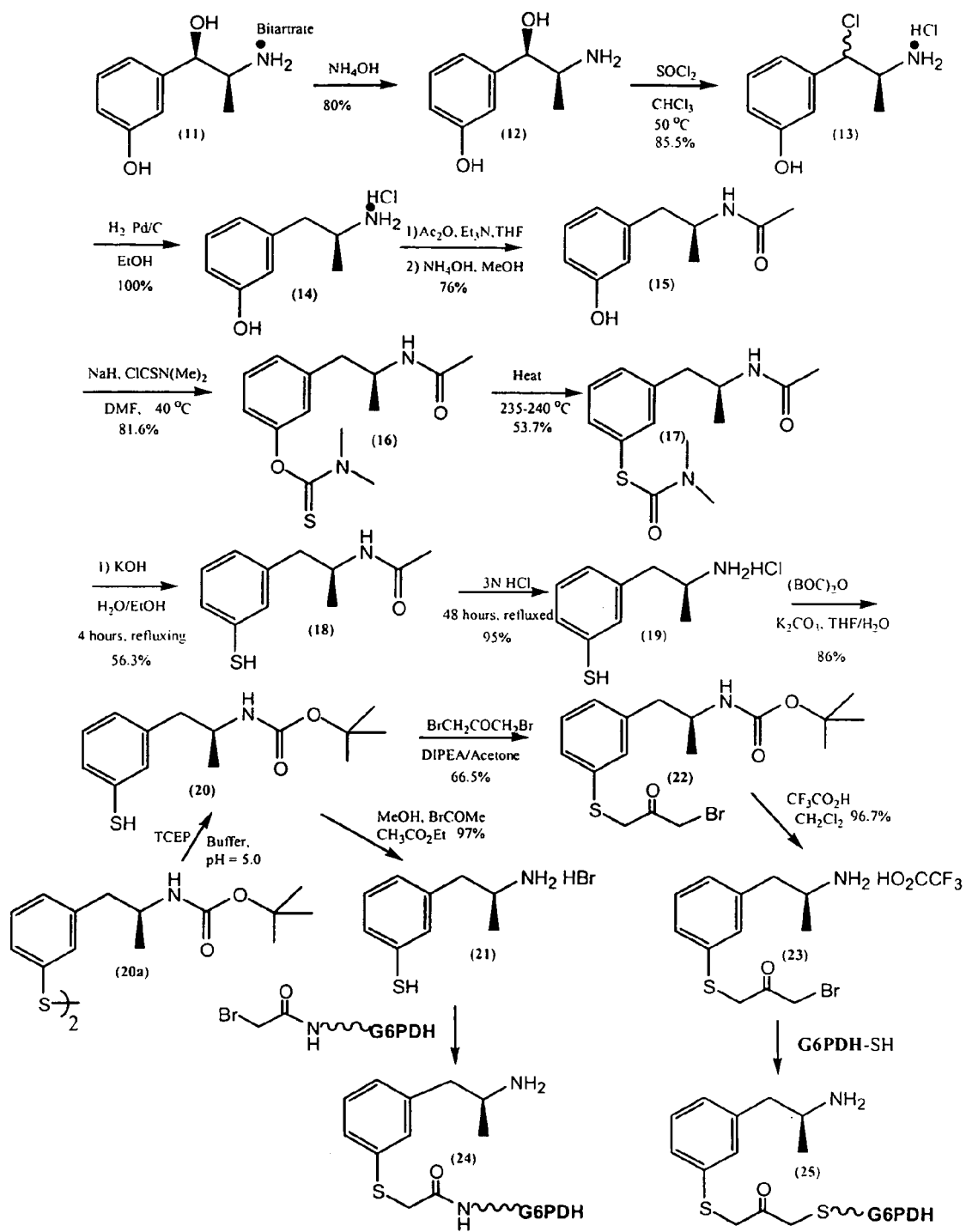
Fig. 1. Syntheses of Steroespecific Amphetamine Haptens (21) and (23)

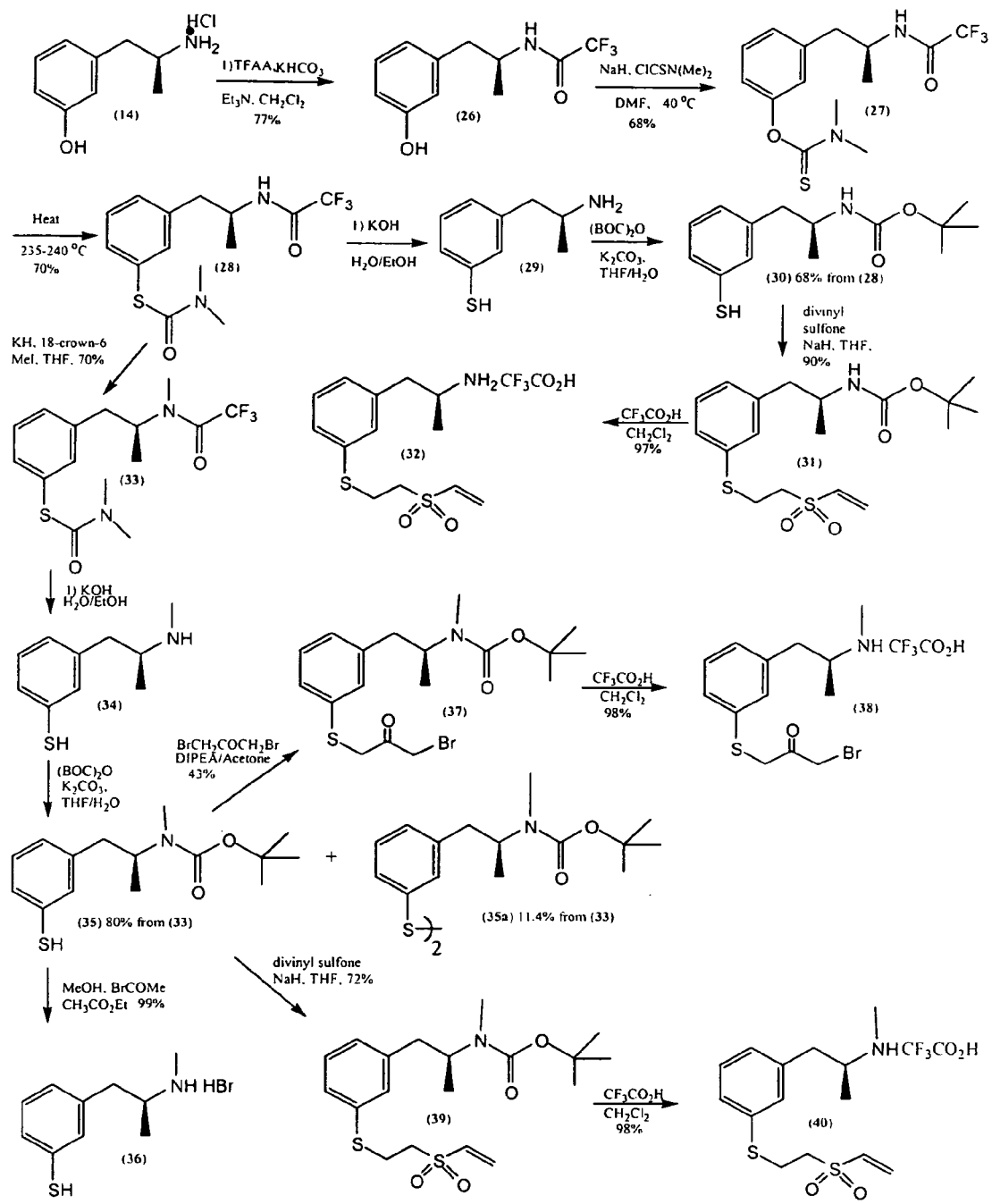
Fig. 2. Syntheses of Steroespecific Amphetamine Haptens (32),(36), (38) and (40)

ASSAYS FOR AMPHETAMINE AND METHAMPHETAMINE USING STEREOSPECIFIC REAGENTS

BACKGROUND OF THE INVENTION

This invention relates to methods, compositions and kits for detecting the presence and/or amounts of amphetamine and/or methamphetamine in samples suspected of containing the same. In particular, the invention relates to bivalent hapten conjugates comprising an amphetamine moiety and a methamphetamine moiety. The conjugate may be employed in assays for amphetamine and/or methamphetamine.

The clinical diagnostic field has seen a broad expansion in recent years, both as to the variety of materials of interest that may be readily and accurately determined, as well as the methods for the determination. Over the last decade, testing for drugs of abuse has become commonplace. This testing is not only for the monitoring of criminal offenders and drug addicts, but employers also use it for the screening of workers. In recent years immunoassays based on the reaction of an antibody with an antigen have been extensively investigated for this purpose.

Typically, immunoassays employ an antibody whose structure recognizes an analyte in a specific manner. The immunoassay is conducted with a signal producing system that produces a detectible change in signal upon binding of the analyte to the antibody. Accordingly, when testing for an analyte in a sample, a detectible change in signal from that produced with a negative sample of a calibrator is taken as a positive result for the presence of that analyte in the sample.

Amphetamine and methamphetamine stimulate the central nervous system and have been used medicinally to treat hypotension, narcolepsy and obesity. D-Methamphetamine is used as desoxyn and its 1-methamphetamine is used in certain non-prescription inhalers as a decongestant. Because of their stimulating effects, the drugs and derivatives have been abused. As a result, assays for the detection of amphetamine and/or methamphetamine in samples are of interest.

A number of assays are available for the screening of urine samples for amphetamine and methamphetamine as drugs of abuse. The present assays have the problem of false positives associated with the presence of many amphetamine-related drugs such as phenmetrazine, phentermine and phenylpropanolamine.

There is, therefore, a need for assays for the detection of amphetamine and/or methamphetamine where the number of false positive results are reduced. The assay should have improved sensitivity and specificity, while maintaining or improving on the speed of the assay.

SUMMARY OF THE INVENTION

One embodiment of the present invention is directed to compounds of the formula:

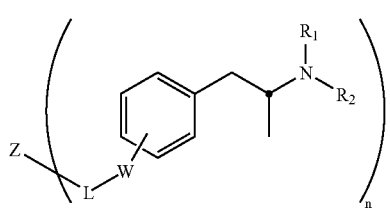

Formula I wherein:
$R^1$ is H, lower alkyl, a protecting group,
$R^2$ is H, lower alkyl, a protecting group,
W is a heteroatom, for example, O, S, $NR^3$ wherein $R^3$ is H or lower alkyl,
L is a bond or a linking group,
Z is H, a protecting group, a poly(amino acid), a non-poly(amino acid) label moiety, a non-poly(amino acid) immunogenic carrier, or a functional group excluding thiol,
n is 1 when Z is other than a poly(amino acid) or, when Z is a poly(amino acid), n is an integer between 1 and the molecular weight of the poly(amino acid) divided by about 500;

and salts thereof.

Another embodiment of the present invention is directed to compounds of the formula:

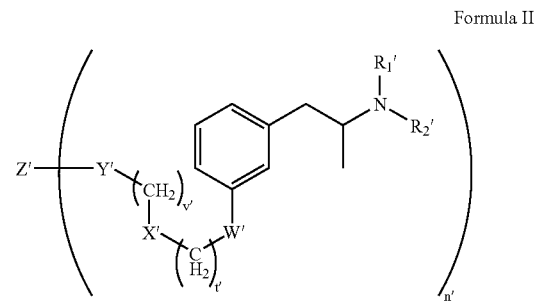

Formula II wherein:
$R^{1'}$ is H, lower alkyl, a protecting group,
$R^{2'}$ is H, lower alkyl, a protecting group,
W' is a heteroatom such as O, S, $NR^{3'}$ wherein $R^{3'}$ is H or lower alkyl,
X' is C(O) or $SO_2$,
Y' is bond, S or $-NR^{3'}$ wherein $R^{3'}$ is H or lower alkyl,
Z' is H, a protecting group, a poly(amino acid), a non-poly(amino acid) label moiety, a non-poly(amino acid) immunogenic carrier, or a functional group,
t' is an integer from 1 to 6 and v' is an integer from 0 to 6,
n' is 1 when Z' is other than a poly(amino acid) or, when Z' is a poly(amino acid), n' is an integer between 1 and the molecular weight of the poly(amino acid) divided by about 500;

and salts thereof.

Another embodiment of the present invention is directed to compounds of Formula II, which are stereoisomers. In one embodiment the stereoisomer has the formula:

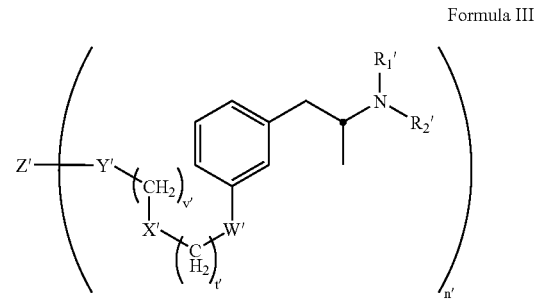

Formula III

Another embodiment of the present invention is directed to compounds of the formula:

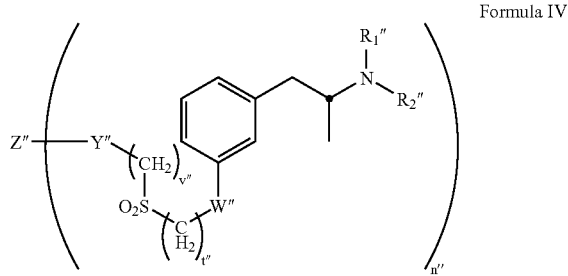

Formula IV wherein:

$R^{1"}$ is H, lower alkyl, a protecting group, $R^{2"}$ is H, lower alkyl, a protecting group, W" is a heteroatom such as O, S, $NR^{3"}$ wherein $R^{3"}$ is H or lower alkyl, Y" is bond, S or $-NR^{3"}$ wherein $R^{3"}$ is H or lower alkyl, Z" is H, a protecting group, a poly(amino acid), a non-poly(amino acid) label moiety, a non-poly(amino acid) immunogenic carrier, or a functional group, t" is an integer from 1 to 6 and v" is an integer from 2 to 6, n" is 1 when Z" is other than a poly(amino acid) or, when Z" is a poly(amino acid), n" is an integer between 1 and the molecular weight of the poly(amino acid) divided by about 500;

and salts thereof.

Another embodiment of the present invention concerns compounds of the formula:

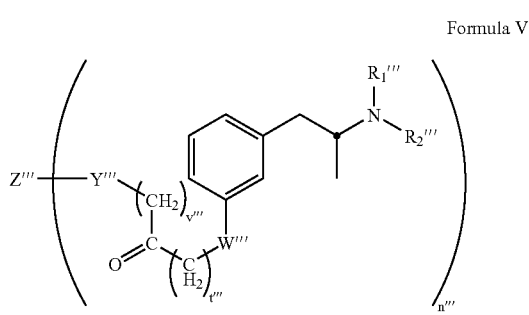

Formula V wherein:

$R^{1'''}$ is H, lower alkyl, a protecting group, $R^{2'''}$ is H, lower alkyl, a protecting group, W''' is a heteroatom such as O, S, $NR^{3'''}$ wherein $R^{3'''}$ is H or lower alkyl, Y''' is a bond, S or $-NR^{3'''}$ wherein $R^{3'''}$ is H or lower alkyl, Z''' is H, a protecting group, a poly(amino acid), a non-poly(amino acid) label moiety, a non-poly(amino acid) immunogenic carrier, or a functional group, t''' is an integer from 1 to 6 and v''' is an integer from 0 to 6, n''' is 1 when Z''' is other than a poly(amino acid) or, when Z''' is a poly(amino acid), n''' is an integer between 1 and the molecular weight of the poly(amino acid) divided by about 500;

and salts thereof.

Other embodiments of the present invention include antibodies raised against the compounds of Formula IV and Formula V wherein Z" or Z''', respectively, are antigens or non-poly(amino acid) immunogenic carriers.

Other embodiments of the present inventions include enzyme conjugates of the compounds of Formula IV and Formula V wherein Z' or Z''', respectively, are enzymes.

Other embodiments of the present invention include reagent systems that comprise one or more of the aforementioned antibodies or enzyme conjugates.

Another embodiment of the present invention is a method for determining amphetamine and/or methamphetamine in a sample suspected of containing amphetamine and/or methamphetamine. The method comprises combining in a medium a sample and one of the aforementioned reagent systems and examining the medium for the presence of a complex comprising the amphetamine and/or methamphetamine and antibody for amphetamine and/or a complex of amphetamine and/or methamphetamine and antibody for methamphetamine. The presence of the complex indicates the presence of amphetamine and/or methamphetamine in the sample.

Another embodiment of the present invention is a kit comprising in packaged combination one or more members of the reagent system as mentioned above.

BRIEF DESCRIPTION OF THE DRAWINGS

FIG. 1 is a reaction scheme depicting an example of a synthesis of certain compounds in accordance with the present invention.

FIG. 2 is a reaction scheme depicting an example of a synthesis of certain compounds in accordance with the present invention.

DESCRIPTION OF THE SPECIFIC EMBODIMENTS

The present invention permits effective screening of samples for the presence of an amphetamine and/or a methamphetamine with a high degree of specificity and sensitivity. The chiral haptens of the invention can be used to prepare immunogens to raise monoclonal antibodies that may be used in reagent systems for the detection of amphetamine and/or methamphetamine. The chiral haptens may also be used to prepare label conjugates, such as enzyme conjugates, for use in such reagent systems. The enzyme conjugates and other conjugates may also be employed to screen monoclonal antibodies for use in the present methods.

The reagent systems or assay compositions of the invention include label conjugates of a stereospecific amphetamine moiety and/or a stereospecific methamphetamine moiety. The reagent systems further include two antibodies, namely, an antibody for amphetamine and an antibody for methamphetamine. The reagent system may be used in methods for detecting the aforementioned drugs in samples suspected of containing the drugs. In the assays the amphetamines, i.e., amphetamine and/or methamphetamine, to be measured are the analytes. In general, an analyte is a ligand and is a member of a specific binding pair, which may be, for example, the ligand or analyte and a corresponding antibody for the ligand or analyte.

Reagent systems or assay compositions comprising compounds of this invention are useful in a wide variety of known general assay methods such as, e.g., immunoassay methods, both homogeneous and heterogeneous. The conditions under which these assays have been carried out will normally be applicable to assays employing the present compounds. Thus, the compositions of this invention can be used in known immunoassays so as to provide a means to determine the presence of amphetamine and/or methamphetamine in a sample suspected of containing amphetamine and/or methamphetamine. By appropriate choice of components for producing a detectible signal, the detectible signal may be observed visually or by means of various apparatus, i.e., detection means, such as spectrophotometers, fluorometers, scintillation counters, etc. The choice of assay or assay protocol usually determines whether an increase or decrease in the amount of signal generated by the signal producing system determines the amount of amphetamines in the assay sample.

In the present invention a stereospecific amphetamine moiety and/or stereospecific methamphetamine moiety is synthesized and conjugated by means of a linking group to an attachable moiety such as, for example, a poly(amino acid), a non-poly(amino acid) label, a non-poly(amino acid) immunogenic carrier and so forth. The linking group typically has at least one functional group for attachment of the amphetamine moiety or methamphetamine moiety and a functional group for subsequent attachment of the attachable moiety. By the term "stereospecific" is meant a stereoisomer of an amphetamine moiety or a methamphetamine moiety. One stereoisomeric or chiral center for both amphetamine and methamphetamine is the amine carbon giving rise to d- and l-stereoisomers.

The term "amphetamine" includes amphetamine (d,l), its wholly or partially racemic forms, as well as stereoisomeric forms, e.g., d and forms and so forth. The term "methamphetamine" includes methamphetamine (d,l), its wholly or partially racemic forms, as well as stereoisomeric forms, e.g., d and l forms and so forth. The phrase "partially racemic" refers to stereoisomerically or enantiomerically purified forms of the above such as a stereoisomeric mixture that comprises at least 51%, at least 55%, at least 60%, at least 65%, at least 70%, at least 75%, at least 80%, at least 85%, at least 90%, at least 95%, at least 96%, at least 97%, at least 98%, at least 99% of one stereoisomeric form over the other.

The stereospecific amphetamine moiety and/or methamphetamine moiety is generally an analog of amphetamine or methamphetamine, respectively. A ligand analog such as an amphetamine moiety and/or methamphetamine moiety is a modified ligand that, as part of a conjugate of the invention, can compete with the analogous ligand or analyte for binding to an antibody. The modification of the analog provides means to join a ligand analog to another molecule such as a linking group and ultimately to an attachable moiety. The ligand analog may differ from the ligand by replacement of a hydrogen with a bond which links the ligand analog to the linking group. The terms "amphetamine moiety" and "methamphetamine moiety" also include derivatives of amphetamine and methamphetamine such as, for example, esters, amides, ethers, amines, alcohols and the like.

One set of derivatives involves moieties wherein the amine functionality of the amphetamine or methamphetamine is protected with a protecting group. Suitable types of protecting groups are well known in the art and have been described in detail in numerous patents and articles in the technical literature. See, for example, "Principles of Peptide Synthesis" (M. Bodanszky, Springer Verlag, Berlin, Heidelberg, N.Y., Tokyo (1984). Such protecting groups include, by way of example and not limitation, t-butoxycarbonyl (t-Boc), fluorenylmethyloxycarbonyl (Fmoc), acetaminomethyl (Acm), triphenyl methyl (Trt), benzyloxycarbonyl, biphenylisopropyloxycarbonyl, 1-amyloxycarbonyl, isobornyl-oxycarbonyl, alpha-dimethyl-3,5-dimethoxybenxyloxycarbonyl, o-nitrophenylsulfenyl, 2-cyano-1,1-dimentyl-ethoxycarbonyl, bromobenzyloxy, carbamyl, formyl, and the like.

In some embodiments, the amphetamine moiety or methamphetamine moiety is linked from a respective phenyl group, in some embodiments, from the 3-position (meta) on the phenyl group. However, the moieties may be linked from other positions of the respective molecules and on the phenyl groups, e.g., from the 2-position (ortho) or 4-position (para), as long as the moieties are specifically recognized by their respective antibodies to the extent necessary to obtain a sensitive and accurate assay for amphetamine and/or methamphetamine. For homogeneous assays there should be sufficient competition between the respective antibodies and the amphetamine moiety and methamphetamine moiety of the conjugate on the one hand and the analyte amphetamine and methamphetamine on the other hand to produce a reliable assay. Furthermore, there should be sufficient inhibition of the label such as enzyme label to achieve an accurate and sensitive assay.

The linking group may comprise about 3 to about 15 atoms, about 3 to about 12 atoms, about 4 to about 10 atoms, not counting hydrogen or the functionality for linking to the second linking group. The linking group usually comprises a chain of 3, 4, 5, 6, 7 or 8 atoms, e.g., from about 3 to about 8 atoms, from about 4 to about 7 atoms, each independently selected from the group normally consisting of carbon, oxygen, sulfur, nitrogen, halogen and phosphorous, and so forth. The number of heteroatoms in the linking group, excluding the functionality for linking to the second linking group, usually ranges from about 0 to 6, usually from about 2 to 5.

The linking group may be aliphatic or aromatic. When heteroatoms are present, oxygen will usually be present as oxo or ether bonded to carbon; sulfur is usually present as a thioether or other functionality that corresponds to an analogous oxygen functionality; nitrogen is usually present as nitro, nitroso or amino, normally bonded to carbon; phosphorous is usually bonded to carbon, sulfur, oxygen or nitrogen, usually as phosphonate and phosphate mono- or diester. Common functionalities in forming a covalent bond between the linking group and the molecule to be conjugated, namely, amphetamine and methamphetamine, include alkylamine, amidine, thioamide, ether, urea, thiourea, guanidine, azo, thioether and carboxylate, sulfonate, and phosphate esters, amides and thioesters.

For the most part, the functionality for linking to the attachable moiety may be a non-oxocarbonyl group including nitrogen and sulfur analogs, a phosphate group, an amino group, a thiol group, a hydroxy group, alkylating agent such as halo or tosylalkyl, oxy (hydroxyl or the sulfur analog, mercapto) oxocarbonyl (e.g., aldehyde or ketone), or active olefin such as a vinyl sulfone or α-,β-unsaturated ester, these functionalities will be linked to amine groups, carboxyl groups, active olefins, alkylating agents, e.g., bromoacetyl. Where an amine and carboxylic acid or its nitrogen derivative or phosphoric acid are linked, amides, amidines and phosphoramides will be formed. Where mercaptan and activated olefin are linked, thioethers will be formed. Where a mercaptan and an alkylating agent are linked, thioethers will be formed. Where aldehyde and an amine are linked under reducing conditions, an alkylamine will be formed. Where a carboxylic acid or phosphate acid and an alcohol are linked, esters will be formed. Various linking groups and linking functionalities are well known in the art; see, for example, Cautrecasas, *J. Biol. Chem.* (1970) 245:3059.

Also included in the above compounds are salts thereof, particularly, salts involving the amine group of the amphetamine and/or methamphetamine. In one embodiment the salts are acid salts, i.e., salts formed with acids such as mineral acids, for example, hydrochloric acid, hydroboric acid and the like, organic acids, for example, trifluoroacetic acid, acetic acid, DL-tartaric acid and so forth.

As mentioned above, one of the attachable moieties is a poly(amino acid). Various protein types are included within the term "poly(amino acid)," both natural and synthetic. These proteins include, for example, enzymes, albumins, serum proteins, e.g., globulins, lipoproteins, and the like. The molecular weight of the poly(amino acids) will generally be at least about 5,000 and have no upper limit, normally being less than 10,000,000, and usually being not more than about 600,000. There will usually be different ranges depending on the type of protein involved. With enzymes, the range will be from about 10,000 to 600,000, and more usually from about 10,000 to 300,000 molecular weight. There is usually at least about 1 amphetamine or methamphetamine analog group per 200,000 molecular weight, more usually at least one per 50,000 molecular weight. In the case of enzymes, the number of amphetamine or methamphetamine analog groups is usually from about 1 to about 20, about 2 to about 15, about 3 to about 12, or about 6 to about 10.

Enzymes of particular interest as labels are redox enzymes, particularly dehydrogenases such as glucose-6-phosphate dehydrogenase, lactate dehydrogenase, etc., and enzymes that involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference. When a single enzyme is used as a label, other enzymes may find use such as hydrolases, transferases, and oxidoreductases, preferably hydrolases such as alkaline phosphatase and beta-galactosidase. Alternatively, luciferases may be used such as firefly luciferase and bacterial luciferase.

Illustrative co-enzymes that find use include NAD[H], NADP[H], pyridoxal phosphate, FAD[H], FMN[H], etc., usually coenzymes involving cycling reactions. See, for example, U.S. Pat. No. 4,318,980, the disclosure of which is incorporated herein by reference.

The term "non-poly(amino acid) labels" are those labels that are not proteins such as enzymes. A non-poly(amino acid) label may be a member of a signal producing system. The non-poly(amino acid) label is capable of being detected directly or is detectable through a specific binding reaction that produces a detectable signal. The non-poly(amino acid) labels generally are radioisotopic, luminescent, particulate, polynucleotidic or the like. More particularly, the label can be isotopic or non-isotopic, usually non-isotopic, and can be a polynucleotide coding for a catalyst, promoter, dye, fluorescent molecule, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like.

The signal producing system may have one or more components, at least one component being the label, whether poly(amino acid) or non-poly(amino acid). The signal producing system generates a signal that relates to the presence of an amphetamine and/or methamphetamine in a sample. The signal producing system includes all of the reagents required to produce a measurable signal. Other components of the signal producing system may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination. Exemplary signal-producing systems are described in U.S. Pat. No. 5,508,178 (Rose, et al.), the relevant disclosure of which is incorporated herein by reference.

Immunogenic carriers include certain poly(amino acids) and non-poly(amino acids). By the term "immunogenic carrier" is meant a group which, when conjugated to a hapten and injected into a mammal, will induce an immune response and elicit the production of antibodies that bind to the hapten. Haptens are compounds capable of binding specifically to corresponding antibodies, but do not themselves act as immunogens (or antigens) for preparation of the antibodies. Antibodies that recognize a hapten can be prepared against compounds comprised of the hapten linked to an immunogenic (or antigenic) carrier. Immunogenic carriers are also referred to as antigenic carriers. Typical immunogenic carriers include, without limitation, poly (amino acids), polysaccharides, nucleic acids and particles (biologic and synthetic materials). A wide variety of such carriers are disclosed in Davalian, et al., U.S. Pat. No. 5,089,390, column 4, line 57 to column 5, line 5, incorporated herein by reference.

The molecular weight range for poly(amino acids) that are immunogenic carriers such as protein antigens is from about 5,000 to 10,000,000, usually from about 20,000 to 600,000, and more usually from about 25,000 to 250,000 molecular weight. Poly(amino acid) immunogenic carriers include proteins such as, for example, albumins, serum proteins, e.g., globulins, ocular lens proteins and lipoproteins, and so forth. Illustrative proteins include bovine serum albumin (BSA), keyhole limpet hemocyanin ("KLH"), egg ovalbumin, bovine gamma-globulin (BGG) and the like. Non-poly (amino acid) immunogenic carriers include polysaccharides, particles, and the like.

As mentioned above, one embodiment of the present invention concerns compounds of the formula:

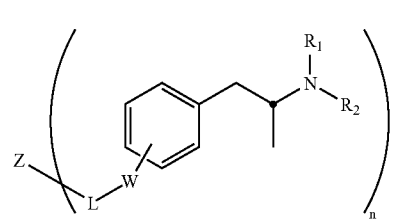

Formula I wherein:

R$^1$ is H, lower alkyl, a protecting group,

R$^2$ is H, lower alkyl, a protecting group,

L is a bond or a linking group,

W is a heteroatom such as, for example, O, S, NR$^3$, e.g., S, attached to the ortho (o-), meta (m-), or para (p-) position of the ring, or the o- or m-position of the ring, or the m-position of the ring, and wherein R$^3$ is H or lower alkyl (1 to 5 carbon atoms), and the like;

Z is H, a protecting group, a poly(amino acid), a non-poly(amino acid) label moiety, a non-poly(amino acid) immunogenic carrier, or a functional group, n is 1 when Z is other than a poly(amino acid) or, when Z is a poly(amino acid), n is an integer between 1 and the molecular weight of the poly(amino acid) divided by about 500.

Salts of the above compounds are also included within the above formula. In one specific embodiment, the linking group L is —(CH$_2$)$_t$—X—(CH$_2$)$_v$—Y— wherein X is C(O) or SO$_2$, Y is a bond, S or —NR$^3$ wherein R$^3$ is H or lower alkyl, and t is an integer from 1 to 6 and v is an integer from 0 to 6.

As used throughout this specification,

represents

or

By the term "lower alkyl" is meant a branched or unbranched saturated monovalent hydrocarbon radical containing 1 to 10, usually, 1 to 5, carbon atoms, such as methyl, ethyl, propyl, butyl and pentyl, and including the normal, secondary, tertiary, and the like, forms thereof where appropriate. The lower alkyl groups may be substituted or unsubstituted.

"Substituted" means that a hydrogen atom of a molecule is replaced by another atom, which may be a single atom such as a halogen, or heteroatom, or part of a group of atoms forming, for example, alkyl groups, heteroatom substituted alkyl groups, cyclic structures or heterocyclic structures.

Another embodiment of the present invention is directed to compounds of the formula:

Formula II

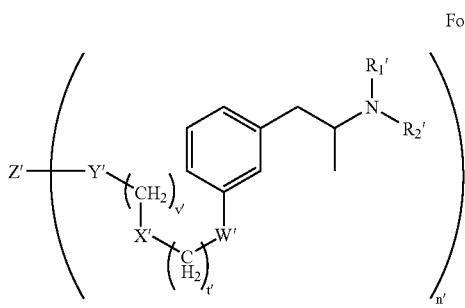

wherein:

R$^{1\prime}$ is H, lower alkyl, a protecting group,
R$^{2\prime}$ is H, lower alkyl, a protecting group,
W' is a heteroatom such as, for example, O, S, NR$^{3\prime}$ and the like, for example, S, and wherein R$^{3\prime}$ is H or lower alkyl,
X' is C(O) or SO$_2$,
Y' is bond, S or —NR$^{3\prime}$ wherein R$^3$ is H or lower alkyl,
Z' is H, a protecting group, a poly(amino acid), a non-poly(amino acid) label moiety, a non-poly(amino acid) immunogenic carrier, or a functional group,
t' is an integer from 1 to 6 and v' is an integer from 0 to 6,
n' is 1 when Z' is other than a poly(amino acid) or, when Z' is a poly(amino acid), n' is an integer between 1 and the molecular weight of the poly(amino acid) divided by about 500.

The compounds also include salts of the above. The compounds of Formula II include racemic compounds, e.g., d,l forms, as well as stereoisomeric compounds, e.g., d and l forms.

In one particular embodiment of the above, the stereoisomer has the formula:

Formula IIIA

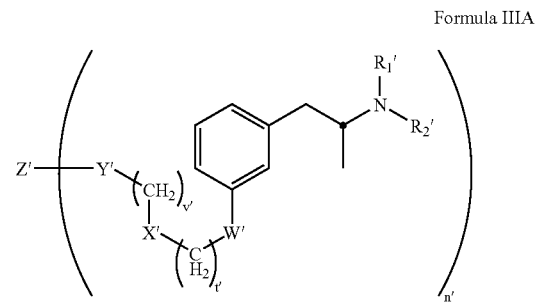

wherein R$_1$' and R$_2$', R$^{3\prime}$, t', X', v', Y' and Z' are as defined above.

In one particular embodiment of the above, the stereoisomer has the formula:

Formula IIIB

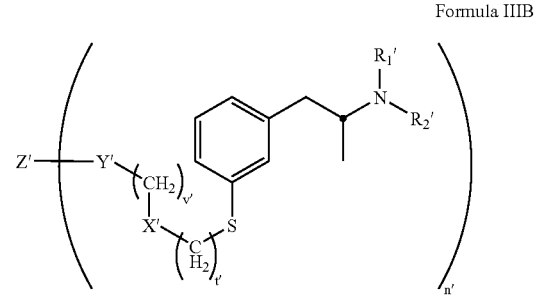

wherein R$_1$' and R$_2$', R$^{3\prime}$, t', X', v', Y' and Z' are as defined above.

Another embodiment of the present invention is directed to compounds of the formula:

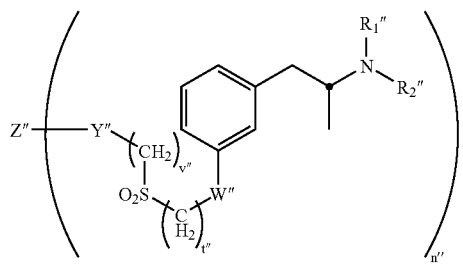

Formula IV wherein:
R$_1$" is H, lower alkyl, a protecting group,
R$_2$" is H, lower alkyl, a protecting group,
W" is a heteroatom such as, for example, O, S, NR$^3$" and the like, for example, S, and wherein R$^3$" is H or lower alkyl,
Y" is bond, S or —NR$^3$" wherein R$^3$" is H or lower alkyl,
Z" is H, a protecting group, a poly(amino acid), a non-poly(amino acid) label moiety, a non-poly(amino acid) immunogenic carrier, or a functional group,
t" is an integer from 1 to 6 and v" is an integer from 2 to 6,
n" is 1 when Z" is other than a poly(amino acid) or, when Z" is a poly(amino acid), n" is an integer between 1 and the molecular weight of the poly(amino acid) divided by about 500.

The compounds also include salts of the above.

In one particular embodiment the compounds are of the formula:

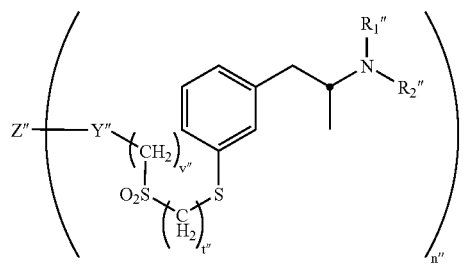

Formula IVA wherein R$_1$" and R$_2$", R$^3$", t", X", v", Y" and Z" are as defined above.

Another embodiment of the present invention concerns compounds of the formula:

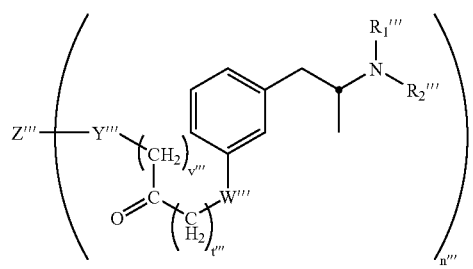

Formula V wherein:
R$^1$''' is H, lower alkyl, a protecting group,
R$^2$''' is H, lower alkyl, a protecting group,
W''' is a heteroatom such as, for example, O, S, NR$^3$''' and the like, for example, S, and wherein R$^3$''' is H or lower alkyl,
Y''' is a bond, S or —NR$^3$''' wherein R$^3$''' is H or lower alkyl,
Z''' is H, a protecting group, a poly(amino acid), a non-poly(amino acid) label moiety, a non-poly(amino acid) immunogenic carrier, or a functional group,
t''' is an integer from 1 to 6 and v''' is an integer from 0 to 6,
n''' is 1 when Z''' is other than a poly(amino acid) or, when Z''' is a poly(amino acid), n''' is an integer between 1 and the molecular weight of the poly(amino acid) divided by about 500;

and salts thereof.

In one particular embodiment of the above, the compounds have the formula:

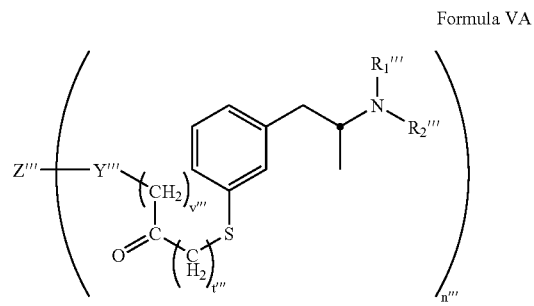

Formula VA wherein R$_1$''' and R$_2$''', R$^3$''', t''', X''', v''', Y''' and Z''' are as defined above.

The synthesis of representative examples of the above compounds is discussed herein by way of illustration and not limitation. Other synthetic procedures will be suggested to those skilled in the art in view of the disclosure herein. Other compounds within the scope of the present invention may be prepared using suitable variants of the reagents employed below.

Stereospecific amphetamine and methamphetamine haptens may be prepared, in general, from a commercially available stereospecific precursor such as, for example, a stereospecific 1-phenyl-2-aminopropane compound having a functional group in the desired position on the phenyl ring such as, e.g., the 3-position. Partially racemic mixtures of the stereoisomers may be prepared as discussed above using corresponding partially racemic mixtures of the precursor compounds. Conjugates of these stereospecific amphetamine and methamphetamine haptens may be prepared, for example, by procedures outlined in FIG. 1 and FIG. 2 wherein the d-stereoisomer is employed by way of illustration and not limitation. Referring to FIG. 1, stereoisomer (11), which is d-1-(3-hydroxyphenyl)-2-aminopropane bitartrate salt is treated first to convert the amino group to the free amine. The nature of the treatment is dependent on the nature of the salt. Usually, such conversion is achieved using basic conditions (pH about 9 to about 14) in an aqueous medium such as, for example, aqueous ammonium hydroxide, aqueous potassium or sodium carbonate, sodium or potassium hydroxide, amines and the like. The aqueous medium may also contain an organic solvent such as, e.g., an alcohol such as methanol, ethanol, isopropanol, and the like.

The reaction temperature is usually about 0° C. to about 50° C., more usually, about 20° C. to about 30° C., preferably, ambient temperature. The reaction is carried out for a period of about 20 minutes to about 1 hour or more, usually, about 25 minutes to about 35 minutes.

The resulting free amine (12) is treated under conditions for thionylation to convert the hydroxy group to a group that may be subsequently reduced such as, e.g., a chlorine, bromine or fluorine group, and the like. The thionylation reagent may be, for example, a thionyl chloride, and the like. The reaction is usually carried out in an organic solvent such as, for example, methylene chloride, trichloromethane, chloroform and so forth. The reaction temperature is usually about 20° C. to about 80° C., more usually, about 45° C. to about 55° C. The reaction is carried out for a period of about 10 minutes to about 3 hours or more, usually, about 40 minutes to about 60 minutes. The resulting product is a salt, in this example, chloride salt, as depicted in compound (13).

Subsequently, compound (13) is treated under reducing conditions such as, for example, hydrogen in the presence of a suitable catalyst, e.g., palladium and charcoal, platinum and charcoal, and so forth to give the (S)-configuration of compound (14). The reaction is usually carried out in an oxygenated organic solvent such as, e.g., an alcohol such as methanol, ethanol, isopropanol, and the like. The pressure of the hydrogen is usually about 20 to about 50 psi, more usually, about 30 to about 40 psi. The reaction temperature is usually about 0° C. to about 30° C., more usually, about 23° C. to about 28° C., preferably, ambient temperature. The reaction is carried out for a period of about 10 hours minutes to about 20 hours or more, usually, about 15 hours to about 17 hours.

Compound (15) is obtained by acylation of compound (14) followed by hydrolysis of the salt. In the example shown compound (15) is treated under acetylation conditions, namely, acetic anhydride in a basic medium such as, for example, mono-, di-, and tri-alkyl amines such as, for example, diisopropylethyl amine, diethyl amine, ethyl amine triethyl amine, and the like. The reaction is carried out in an organic solvent such as, e.g., a ketone, e.g., acetone and the like, an organic ether, e.g., ethyl ether, tetrahydrofuran (THF), and the like, an alcohol, e.g., methanol, ethanol, propanol, and the like. The reaction temperature is usually about 0° C. to about 50° C., more usually, about 10° C. to about 30° C., preferably, ambient temperature. The reaction is carried out for a period of about 10 minutes to about 3 hours or more, usually, about 30 minutes to about 60 minutes. The resulting product is hydrolyzed to produce compound (15). Usually, such conversion is achieved using basic conditions (pH about 13 to about 15, about 14) in an aqueous medium such as, for example, aqueous ammonium hydroxide, aqueous potassium or sodium carbonate, potassium or sodium hydroxide, and the like. The aqueous medium may also contain an organic solvent such as, e.g., an alcohol such as methanol, ethanol, propanol, and the like. The reaction temperature is usually about 0° C. to about 50° C., more usually, about 10° C. to about 30° C., preferably, ambient temperature. The reaction is carried out for a period of about 10 minutes to about 3 hours or more, usually, about 30 minutes to about 60 minutes.

Thiocarbamate (16) is produced from compound (15) by treatment of (15) with, for example, dimethyl thiocarbamoyl chloride, in the presence of a metal hydride, e.g., sodium hydride, potassium hydride, calcium hydride and the like. The reaction is carried out in an organic solvent such as, for example, an amide, e.g., dimethylformamide, an ether, for example, diethyl ether, tetrahydrofuran, and the like. Usually, the metal hydride is added initially to a solution of compound (15) and the mixture is stirred for about 10 to about 90 minutes, usually about 40 to about 50 minutes. The reaction mixture is initially at a temperature of about −10° C. to about 10° C., usually, about 0° C. Then, the reaction mixture is stirred at a temperature of about 10° C. to about 40° C., more usually, at ambient temperature. Then, the reaction mixture is cooled to a temperature of about −10° C. to about 10° C., usually, about 0° C., and the dimethyl thiocarbamoyl chloride is added. The reaction temperature is then raised to about 10° C. to about 80° C., more usually, about 40° C. to about 50° C., preferably, ambient temperature. The reaction is carried out for a period of about 1 hour to about 5 hours or more, usually, about 1 hour to about 3 hours.

Next, compound (16) is subjected to conditions for causing rearrangement to yield compound (17), which has a sulfur atom at the 3-position of the phenyl ring. Suitable conditions include, for example, heating compound (16), under an inert gas such as a noble gas, at a temperature sufficient to cause the desired rearrangement, e.g., about 200° C. to about 275° C., usually, about 230° C. to about 245° C.

Compound (17) is hydrolyzed to give compound (18) having a free thiol group. Hydrolysis is usually carried out under an inert gas under basic conditions that are sufficient to give the free thiol. The base may be organic or inorganic. Suitable bases include potassium hydroxide, sodium hydroxide, potassium carbonate, sodium carbonate, and the like in aqueous organic solvent such as an oxygenated organic solvent, e.g., an alcohol (methanol, ethanol, and the like), an ether (tetrahydrofuran, diethyl ether, and the like). The reaction temperature is usually about 0° C. to about 110° C., more usually, about 78° C. to about 100° C., preferably, at reflux temperature. The reaction is carried out for a period of about 5 minutes to about 24 hours or more, usually, about 3 hours to about 5 hours. As can be seen, the acetamine group is not removed under the above conditions.

Accordingly, compound (18) is subjected to conditions for removing the acetamine group to give compound (19) having a free amine group. In general, acidic conditions are employed sufficient to hydrolyze the acetamine group and the reaction is usually carried out under an inert gas. The acid may be organic or inorganic. Inorganic acids include mineral acids such as, for example, hydrochloric acid, sulfuric acid, and the like. The reaction temperature is usually about 0° C. to about 150° C., more usually, about 100° C. to about 125° C., preferably, at reflux temperature. The reaction is carried out for a period of about 1 hour to about 200 hours or more, usually, about 30 hours to about 60 hours. The resulting product, compound (19), is in the form of the acid salt (hydrochloric acid salt in the example shown).

The amine group on compound (19) is then protected to give compound (20). Suitable protecting groups are well known in the art and have been described in detail in numerous patents and articles in the technical literature. See, for example, "Principles of Peptide Synthesis" (M. Bodanszky, Springer Verlag, Berlin, Heidelberg, N.Y., Tokyo (1984). Examples of such protecting groups, by way of example and not limitation, are t-butoxycarbonyl (t-Boc), fluorenylmethyloxycarbonyl (Fmoc), acetaminomethyl (Acm), triphenyl methyl (Trt), benzyloxycarbonyl, biphenylisopropyloxycarbonyl, 1-amyloxycarbonyl, isobornyloxycarbonyl, alpha-dimethyl-3,5-dimethoxybenzyloxycarbonyl, o-nitrophenylsulfenyl, 2-cyano-1,1-dimentylethoxycarbonyl, bromobenzyloxy, carbamyl, formyl, and the like. The particular protecting group chosen depends on the nature of the reaction to be performed and the conditions of such reaction such as temperature, pH, and so forth.

Referring again to FIG. 1, the protecting group employed in this exemplary synthesis is di-tert-butyldicarbonate ((tBoc)$_2$O) in an aqueous organic solvent such as an ether, e.g., THF and the like. A suitable carbonate such as potassium carbonate, sodium carbonate, and the like, is included in the reaction medium to provide for basic conditions. The reagents are usually combined at a temperature of about −10° C. to about 10° C. The reaction temperature is usually about 10° C. to about 50° C., more usually, about 20° C. to about 30° C., preferably, ambient temperature. The reaction is usually carried out under an inert gas and conducted for a period of about 30 minutes to about 5 hours or more, usually, about 1 hour to about 3 hours.

Enzyme conjugates may be prepared from compounds in accordance with the present invention. In general, functional groups suitable for attaching the compound to the enzyme are usually an activated ester or alkylating agent when the amino acid(s) that are to be conjugated on the enzyme have amino or hydroxyl groups and are usually alkylating agents or the like when the amino acid(s) that are to be conjugated on the enzyme comprise a sulfur atom such as, e.g., a cysteine. A large number of suitable functional groups are available for attaching to amino groups and alcohols such as activated esters including imidic esters, sulfonic esters and phosphate esters, activated nitriles, aldehydes, ketones, alkylating agents and the like. Conjugation of haptens to proteins using these and other attaching groups are well known in the art and are described in reviews such as for example, Maggio, E. T. "Enzyme-Immunoassay" (CRC Press, Boca Raton, Fla., 1980), Chapter 4, which contains an assortment of conjugation techniques; pages 81–88 of which are incorporated herein by reference.

Following reaction of the enzyme with a compound such as discussed above to form a conjugate, the product is then optionally purified as may be required. The purification and characterization of poly(amino acid)-hapten conjugates has been described in detail Maggio, et al.; "enzyme-immunoassay" (CRC Press, Boca Raton, Fla., 1980), Chapter 4, pages 86–88 of which are incorporated herein by reference. For example, if the conjugate is a mutant G6PDH-hapten conjugate, the purification can be by dialysis against aqueous/organic and aqueous solutions such as water/DMF or water, or by gel filtration chromatography on supports such as Sephadex, and the like.

As mentioned above, the conjugation can involve binding of a hapten to a free thiol group present on an amino acid side chain of the enzyme (e.g. cysteine). Such conjugation involves alkylation of the thiol sulfur atom by treatment with an electrophilic compound such as an alpha- or beta-unsaturated amide, ketone, ester, or the like, or an alkylating agent such as a reactive halide, e.g., bromide, or sulfonate or the like or reaction with an active disulfide such as a 2-nitro-4-carboxyphenyl disulfide. Specific examples by way of illustration and not limitation include alpha-bromoamides, maleimides, vinyl sulfones, alpha-iodoketones, and the like.

Conjugation reactions with enzymes can be affected by a number of factors. These include, but are not confined to, pH, temperature, buffer, ionic strength, substances which may protect the enzyme active site, amount and type of cosolvent, reaction time, and activation chemistry. A range of pH values from about 5.0 to about 9.5 can usually be used for conjugation reactions. These reactions are generally carried out at about 0 to about 40 degrees C., preferably about 4 to about 20 degrees C.

A number of buffers and salts, both alone and in combination, can be used for such reactions. These include Tris, bicarbonate, phosphate, pyrophosphate, EDTA, KCl, NaCl, and many others. The active site may be protected by substrates (i.e. glucose-6-phosphate for glucose-6-phosphate dehydrogenase), cofactors (NAD$^+$, NADH, NADP$^+$, NADPH) and cofactor analogs (thio-NAD$^+$, thio-NADH, thio-NADP$^+$, or thio-NADPH), and compounds that react reversibly with lysine (i.e. pyridoxal) to reduce deactivation of the enzyme during conjugation.

Cosolvents which may enhance hapten solubility include, but are not limited to, dimethylformamide, carbitol, dimethyl sulfoxide, 1-Methyl-2-pyrrolidinone, and 1,3-Dimethyl-3,4,5,6-tetrahydro 2(1H)-pyrimidinone. These may be useful as about 1 to about 30% of the reaction volume. Reactions can vary from about 15 minutes to many days, depending on the activation chemistry. Carboxylic compounds may be activated to form esters with N-Hydroxysuccinimide or its sulfo-analog, or to mixed anhydrides through reaction with carbitol chloroformate or t-butylchloroformate, or may be coupled directly using carbodiimides such as EDAC. For reaction with cysteine thiols on the enzyme, the hapten should contain a good leaving group such as I, Br or tosyl; alternatively, the hapten can contain a thiol, preferably activated with 2,2' dithiodipyridine or DTNB.

Another method of conjugation, described in Rowley, G. L., D. Leung, and P. Singh (U.S. Pat. No. 4,220,722) involves modification of the enzyme with bromoacetyl containing reactants; the bromo groups are subsequently reacted with thiol-containing haptens. The reaction of enzyme with bromoacetyl modifier, and the bromoacetyl enzyme with the thiolated hapten, are subject to the same reaction condition variables described above.

Referring to FIG. 1, compound (20) may be employed to synthesize an enzyme conjugate. In one exemplary approach, compound (20) is treated to remove the protecting group and produce the amine salt. The nature of the conditions for removal is dependent on the nature of the protecting group. In the example depicted, compound (20) is treated with acetyl bromide in an organic solvent, which may be a single solvent or a mixture of organic solvents. Exemplary organic solvents include oxygenated organic solvents such as, e.g., an alcohol such as methanol, ethanol, propanol, etc., a ketone, e.g., acetone, etc., an organic ether, e.g., ethyl ether, tetrahydrofuran (THF), dioxane, etc., an ester, e.g., ethyl acetate, propyl acetate, etc., and the like. The reaction temperature is usually about −70° C. (minor) to about 40° C., more usually, about −20° C. to about 25° C., preferably, ambient temperature. The reaction is carried out for a period of about 2 minutes to about 8 hours or more, usually, about 30 minutes to about 180 minutes. In the synthesis of FIG. 1, amine bromide salt (21) is produced. Compound (21) is then reacted with an enzyme to form an enzyme conjugate, for example, compound (24). In this particular exemplary synthesis, the bromoacetyl derivative of glucose-6-phosphate dehydrogenase (G6PDH) reacts with the free thiol group on compound (21).

In another approach (FIG. 1) the thiol group of compound (20) is treated to form a halo-ketone derivative, namely, compound (22). To this end, compound (20) is treated with an excess of a halo-ketone, for example, 1,3-dibromoacetone, in the presence of an organic base such as a mono-, di-, and tri-alkyl amine, for example, diisopropyl ethyl amine (DIPEA). Other suitable bases include ethyl amine, diethyl amine, triethyl amine, and the like. The reaction is usually carried out in an organic solvent such as, for example, a ketone, e.g., acetone and the like, an organic ether, e.g., ethyl ether, tetrahydrofuran (THF), and the like, an alcohol, e.g., methanol, ethanol, propanol, and the like. The reaction temperature is usually about 0° C. to about 50° C., more usually, about 10° C. to about 30° C., preferably, ambient temperature. The reaction is carried out for a period of about 10 minutes to about 3 hours or more, usually, about 30 minutes to about 60 minutes.

The protecting group of compound (22) may be removed under acidic conditions in an organic solvent to give compound (23). In the example depicted, compound (22) is treated with trifluoroacetic acid (TFA) in a halogenated organic solvent such as, e.g., methylene chloride. In general, removal of the protecting group is dependent on the nature of the protecting group. Suitable conditions for removal of protecting groups are well known in the art and will not be discussed in detail herein. Compound (23) is reacted with an enzyme under conditions where a free thiol group on the enzyme reacts with the halo-ketone functionality to form enzyme conjugate (25). This type of reaction is discussed in more detail above.

Another synthetic approach is presented in FIG. 2 by way of illustration and not limitation. Compound (14) is subjected to conditions for forming an acetyl derivative (26). In the example shown compound (14) is treated with trifluoroacetic anhydride in a basic medium. The solvent employed may be a halogenated organic solvent such as, for example, methylene chloride, trichloromethane, diethyl ether, tetrahydrofuran, and the like. The reaction is carried out in the presence of a base, which may be an inorganic base or an organic base or mixtures thereof. For example, an organic base such as a mono-, di-, and tri-alkyl amine, for example, diisopropyl ethyl amine (DIPEA), ethyl amine, diethyl amine triethyl amine and the like may be employed. Inorganic bases include, for example, potassium carbonate, sodium carbonate, sodium hydroxide, potassium hydroxide, and so forth. The reaction temperature is usually about 0° C. to about 50° C., more usually, about 20° C. to about 30° C., preferably, ambient temperature. The reaction is carried out for a period of about 30 minutes to about 8 hours or more, usually, about 3 hours to about 5 hours.

Compound (26) is converted to a thiocarbamate, compound (27) by treatment with, for example, dimethyl thiocarbamoyl chloride, in the presence of a metal hydride, e.g., sodium hydride, potassium hydride, calcium hydride, and the like. The reaction conditions and reagents are similar to those described above for the conversion of compound (15) to compound (16). Compound (27) is treated to provide for rearrangement to introduce a thio functionality at the 3-position of the phenyl ring and produce compound (28). The conditions and reagents are similar to those described above for the rearrangement of compound (16) to compound (17). Compound (28) is treated to produce compound (29) having a free thiol group. Conditions and reagents are similar to those discussed above for the hydrolysis of compound (17) give compound (18) having a free thiol group. As can be seen, the trifluoroacetamine group is also removed under the above conditions. The amine group on compound (29) is then protected to give compound (30) in a manner similar to that described above.

For the preparation of vinyl sulfone (31), compound (30) is reacted with a sulfone such as divinyl sulfone, and the like. The reaction is conducted under basic conditions, which include a metal hydride such as, for example, sodium hydride, lithium aluminum hydride, potassium hydride, calcium hydride, and the like. The reaction is usually carried out in an organic solvent such as, for example, an ether, e.g., ethyl ether, tetrahydrofuran (THF), dioxane, and the like. The reaction temperature is usually about −20° C. to about 30° C., more usually, about 0° C. to about 10° C. The reaction is carried out for a period of about 10 minutes to about 3 hours or more, usually, about 30 minutes to about 60 minutes. Compound (32) is produced by treatment of compound (31) to remove the protecting group. In the example shown in FIG. 2, the reagents employed are trifluoroacetic acid in a halogenated hydrocarbon solvent such as, e.g., methylene chloride and the like. The conditions are similar to those described above for compound (22).

In another approach compound (28) is treated to introduce a methyl group on the amine group to give compound (33). In one approach, by way of example, methylation may be realized by reacting compound (28) with a methyl halide such as, for example, methyl iodide in the presence of a metal hydride such as, for example, sodium hydride, potassium hydride, calcium hydride, and the like. The reaction is usually carried out in an organic solvent such as, for example, an ether, e.g., ethyl ether, tetrahydrofuran (THF), a crown ether, and the like. The reaction temperature is usually about 0° C. to about 100° C., more usually, about 30° C. to about 70° C. The reaction mixture may be held at ambient temperature for a period of about 10 minutes to about 3 hours or more, usually, about 90 minutes to about 150 minutes and then refluxed for a period of about 10 to about 20 hours, usually about 14 to about 18 hours.

Compound (33) is subjected to conditions for producing free amine and free thiol groups. The conditions and reagents for this step are similar to those described above for the conversion of compound (28) to compound (29). The resulting product, compound (34), is treated to introduce a protecting group on the amine functionality to give compound (35). The conditions and reagents for this step are similar to those discussed above for compound (29).

Compound (35) may be used to produce several compounds for reaction to form protein conjugates. In one approach compound (35) is treated in a manner similar to that discussed above for compound (20) to introduce bromoacetonyl group on the thiol functionality and produce compound (37). Compound (38) is derived from compound (37) by removal of the protecting group in a manner similar to that discussed above for compound (22) discussed above.

In another approach compound (35) is treated in a manner similar to that described above for the formation of compound (21) from compound (20) to yield compound (36).

In another approach divinyl sulfone derivative (39) is obtained from compound (35) in a manner similar to that described above for the conversion of compound (30) to compound (31). Furthermore, compound (40) is obtained from compound (39) in a manner similar to that discussed above for the conversion of compound (31) to compound (32).

Any of the compounds discussed above may be purified by known techniques such as, for example, dialysis, chromatography, and combinations thereof.

Compounds (36), (38) and (40) are employed to form derivatives that comprise poly(amino acids), non-poly (amino acid) immunogenic carriers, non-poly(amino acid) labels, and so forth. For example, these compounds may be reacted with enzymes such as G6PDH and the like to form enzyme conjugates or reacted with immunogenic proteins such as KLH, BSA, and the like to form immunogens.

The immunogenic conjugates of the present invention are employed to prepare antibodies for a stereospecific amphetamine or a stereospecific methamphetamine for the detection of an amphetamine and/or a methamphetamine in a sample suspected of containing the same. The antibodies specific for amphetamine and specific for methamphetamine for use in immunoassays can be monoclonal or polyclonal. Such antibodies can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies.

Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Antiserum containing antibodies (polyclonal) is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7: 1–24 (1975); Broughton and Strong, Clin. Chem. 22: 726–732 (1976); and Playfair, et al., Br. Med. Bull. 30: 24–31 (1974).

Antibodies can also be obtained by somatic cell hybridization techniques, such antibodies being commonly referred to as monoclonal antibodies. Monoclonal antibodies may be produced according to the standard techniques of Köhler and Milstein, Nature 265:495–497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3–46 (1981). Samples of an appropriate immunogen preparation are injected into an animal such as a mouse and, after a sufficient time, the animal is sacrificed and spleen cells obtained. Alternatively, the spleen cells of a non-immunized animal can be sensitized to the immunogen in vitro. The spleen cell chromosomes encoding the base sequences for the desired immunoglobulins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Köhler and Milstein, supra).

In another approach for the preparation of antibodies the sequence coding for antibody binding sites can be excised from the chromosome DNA and inserted into a cloning vector, which can be expressed in bacteria to produce recombinant proteins having the corresponding antibody binding sites.

In general, antibodies can be purified by known techniques such as chromatography, e.g., DEAE chromatography, ABx chromatography, and the like, filtration, and so forth.

The label conjugates and/or antibodies of the present invention may be employed in reagent systems for conducting various assay formats. Such assays usually involve reactions between binding partners such as an amphetamine analyte and/or a methamphetamine analyte and a corresponding antibody or the binding between an antibody and a corresponding binding partner such as a second antibody that binds to the first antibody. Accordingly, the binding partner may be a protein, which may be an antibody or an antigen. The binding partner may be a member of a specific binding pair ("sbp member"), which is one of two different molecules, having an area on the surface or in a cavity, which specifically binds to and is thereby defined as complementary with a particular spatial and polar organization of the other molecule. The members of the specific binding pair will usually be members of an immunological pair such as antigen-antibody, although other specific binding pairs such as biotin-avidin, hormones-hormone receptors, enzyme-substrate, nucleic acid duplexes, IgG-protein A, polynucleotide pairs such as DNA-DNA, DNA-RNA, and the like are not immunological pairs but are included within the scope of sbp member.

Accordingly, specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules. Preferred binding partners are antibodies.

The aforementioned reagents may be employed in all types of immunoassays to determine the presence and/or amount of amphetamine analytes and/or methamphetamine analytes in a sample suspected of containing such analytes. Such assays include, for example, enzyme immunoassays, fluorescence polarization immunoassays, radioimmunoassay, and so forth.

One general group of immunoassays includes immunoassays using the labeled conjugates of the invention with a limited concentration of antibody. Another group of immunoassays involves the use of an excess of all of the principal reagents. Such assays include two-site sandwich assays, e.g., immunoradiometric assays, immunofluorometric assays, immunochemi-luminometric assays, ELISA assays, and so forth. Another group of immunoassays are separation-free homogeneous assays in which the labeled reagents modulate the label signal upon antigen-antibody binding reactions. Another group of assays includes labeled antibody reagent limited competitive assays for hapten or antigen that avoid the use of problematic labeled antigens or haptens. In this type of assay, it is important that the solid phase immobilized analyte be present in a constant, limited amount. The partition of a label between the immobilized analyte and free analyte depends on the concentration of analyte in the sample.

The assays can be performed either without separation (homogeneous) or with separation (heterogeneous) of any of the assay components or products. Homogeneous immunoassays are exemplified by the EMIT® assay (Syva Company, San Jose, Calif.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; and so forth.

Other enzyme immunoassays are the enzyme modulate mediated immunoassay ("EMMIA") discussed by Ngo and Lenhoff, FEBS Lett. (1980) 116:285–288; the substrate labeled fluorescence immunoassay ("SLFIA") disclosed by Oellerich, J. Clin. Chem. Clin. Biochem. (1984) 22:895–904; the combined enzyme donor immunoassays ("CEDIA") disclosed by Khanna, et al., Clin. Chem. Acta (1989) 185:231–240; homogeneous particle labeled immunoassays such as particle enhanced turbidimetric inhibition immunoassays ("PETINIA"), particle enhanced turbidimetric immunoassay ("PETIA"), etc.; and the like.

Exemplary of heterogeneous assays are the enzyme linked immunosorbant assay ("ELISA") discussed in Maggio, E. T. supra; the radioimmunoassay, disclosed in Yalow, et al., *J. Clin. Invest.* 39:1157 (1960) and so forth.

The above reagents may also be employed in multi-analyte immunoassays where the amphetamine and/or methamphetamine analytes may be the subject of detection along with one or more other analytes such as other drugs of abuse and the like. Such multi-analyte systems are described, for example, in Loor, et al., *J. Anal. Toxicol.* 12: 299 (1988).

The homogeneous or heterogeneous assays, particularly enzyme immunoassays and fluorescence polarization immunoassays, are normally carried out in an aqueous buffered medium at a moderate pH, generally that which provides optimum assay sensitivity. The aqueous medium may be solely water or may include from 0 to about 40 volume percent of a cosolvent. The pH for the medium will usually be in the range of about 4 to about 11, more usually in the range of about 5 to about 10, and preferably in the range of about 6.5 to about 9.5. The pH will usually be a compromise between optimum binding of the binding members of any specific binding pairs, the pH optimum for other reagents of the assay such as members of the signal producing system, and so forth.

Various buffers may be used to achieve the desired pH and maintain the pH during the determination. Illustrative buffers include borate, phosphate, carbonate, tris, barbital and the like. The particular buffer employed is not critical to this invention, but in an individual assay one or another buffer may be preferred. Various ancillary materials may be employed in the method in accordance with the present invention. For example, in addition to buffers the medium may comprise stabilizers for the medium and for the reagents employed. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; or the like.

One or more incubation periods may be applied to the medium at one or more intervals including any intervals between addition of various reagents mentioned above. The medium is usually incubated at a temperature and for a time sufficient for binding of various components of the reagents to occur. Moderate temperatures are normally employed for carrying out the method and usually constant temperature, preferably, room temperature, during the period of the measurement. Incubation temperatures normally range from about 5° to about 99° C., usually from about 15° C. to about 70° C., more usually 20° C. to about 45° C. The time period for the incubation is about 0.2 seconds to about 6 hours, usually, from about 2 seconds to about 1 hour, more usually, about 1 to about 5 minutes. The time period depends on the temperature of the medium and the rate of binding of the various reagents, which is determined by the association rate constant, the concentration, the binding constant and dissociation rate constant. Temperatures during measurements will generally range from about 10 to about 50° C., more usually from about 15 to about 40° C.

The concentration of analyte that may be assayed generally varies from about $10^{-5}$ to about $10^{-17}$ M, more usually from about $10^{-6}$ to about $10^{-14}$ M. Considerations, such as whether the assay is qualitative, semi-quantitative or quantitative (relative to the amount of analyte present in the sample), the particular detection technique and the concentration of the analyte normally determine the concentrations of the various reagents.

The concentration of analytes to be detected will generally vary from about $10^{-5}$ to about $10^{-17}$ M, more usually from about $10^{-6}$ to about $10^{-14}$ M. In general, a predetermined cut-off level is established for each analyte suspected of being in a sample. The particular predetermined cut-off level generally is determined on an analyte by analyte basis. Those skilled in the art are well aware of the factors relating to the selection of predetermined cut-off levels. For example, for many drugs of abuse, the cut-off levels are determined by SAMSA, an agency of the Department of Health and Human Services. The nature of the signal producing system may be a consideration in determining the predetermined cut-off levels of some analytes. Another consideration is that the expected variation in concentration of the analytes that is of significance should provide an accurately measurable signal difference.

The concentrations of the various reagents in the assay medium will generally be determined by the concentration range of interest of the amphetamine and/or the methamphetamine analytes. However, the final concentration of each of the reagents is normally determined empirically to optimize the sensitivity of the assay over the range. That is, a variation in concentration of analyte that is of significance should provide an accurately measurable signal difference. Considerations such as the nature of the signal producing system and the nature of, and predetermined cut-off levels for, the analytes normally determine the concentrations of the various reagents.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially. Optionally, an incubation step may be involved subsequent to each addition, generally ranging from about 30 seconds to about 6 hours, more usually from about 1 minute to about 1 hour.

The following examples further describe the specific embodiments of the invention by way of illustration and not limitation and are intended to describe and not to limit the scope of the invention.

In a homogeneous assay after all of the reagents have been combined, the signal is determined and related to the amount of analyte in the sample. For example, in an EMIT assay for amphetamine and/or methamphetamine, a sample suspected of containing amphetamine and/or methamphetamine analytes is combined in an aqueous medium either simultaneously or sequentially with an enzyme conjugate of a stereospecific amphetamine and/or an enzyme conjugate of a stereospecific methamphetamine of the invention and antibody capable of recognizing amphetamine and antibody capable of recognizing methamphetamine where the antibodies also bind to the respective amphetamine and methamphetamine moieties of the enzyme conjugates prepared in accordance with the present invention. Generally, a substrate for the enzyme is added, which results in the formation of a chromogenic or fluorogenic product upon enzyme catalyzed reaction. Preferred enzymes are glucose-6-phosphate dehydrogenase and alkaline phosphatase but other enzymes may be employed. The analytes and the moieties of the enzyme conjugate compete for binding sites on the antibody. The enzyme activity in the medium is then determined, usually by spectrophotometric means, and is compared to the enzyme activity determined when calibrators or reference samples are tested in which a known amount of the analytes is present. Typically, the calibrators are tested in a manner similar to the testing of the sample suspected of containing the analytes. The calibrators typically contain differing, but known, concentrations of the analyte to be determined. Preferably, the concentration ranges present in the calibrators span the range of suspected analyte concentrations in the unknown samples.

The aforementioned assays may be carried out using mutant glucose-6-phosphate dehydrogenase as the enzyme of the enzyme conjugate. This mutant enzyme is described in U.S. Pat. Nos. 6,090,567 and 6,033,890, the relevant disclosures of which are incorporated herein by reference. Furthermore, the assay may be conducted using procedures and amphetamine antibodies and methamphetamine antibodies as disclosed in U.S. Pat. Nos. 5,328,828 and 5,135,863, the relevant disclosures of which are incorporated herein by reference.

Heterogeneous assays usually involve one or more separation steps and can be competitive or non-competitive. A variety of competitive and non-competitive assay formats are disclosed in Davalian, et al., U.S. Pat. No. 5,089,390, column 14, line 25 to column 15, line 9, incorporated herein by reference. In one type of competitive assay a support having antibodies for amphetamine and for methamphetamine bound thereto is contacted with a medium containing the sample and appropriate enzyme conjugates of the invention. After separating the support and the medium, the enzyme activity of the support or the medium is determined by conventional techniques and related to the amount of amphetamine and/or methamphetamine in the sample.

The support may be comprised of an organic or inorganic, solid or fluid, water insoluble material, which may be transparent or partially transparent. The support can have any of a number of shapes, such as particle, including bead, film, membrane, tube, well, strip, rod, plate and the like. Depending on the type of assay, the support may or may not be suspendable in the medium in which it is employed. Examples of suspendable supports are polymeric materials such as latex, lipid bilayers or liposomes, oil droplets, cells and hydrogels. Other support compositions include polymers, such as nitrocellulose, cellulose acetate, poly (vinyl chloride), polyacrylamide, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials.

Binding of components to the surface of a support may be direct or indirect, covalent or non-covalent and can be accomplished by well-known techniques, commonly available in the literature, as discussed above. See, for example, "Immobilized Enzymes," Ichiro Chibata, Halsted Press, New York (1978) and Cautrecasas, *J. Biol. Chem.*, 245:3059 (1970). The surface of the support is usually polyfunctional or be capable of being polyfunctionalized or be capable of binding to an sbp member, or the like, through covalent or specific or non-specific non-covalent interactions. Such binding is indirect where non-covalent interactions are used and is direct where covalent interactions are employed. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to surfaces is well known and is amply illustrated in the literature (see above).

Activation of the signal producing system depends on the nature of the signal producing system members. For those members of a signal producing system that are activated with light, the member is irradiated with light. For members of signal producing systems that are on the surface of a particle, addition of a base may result in activation. Other activation methods will be suggested to those skilled in the art in view of the disclosures herein. For some signal producing systems no agent for activation is necessary such as those systems that involve a label that is a radioactive label, an enzyme, and so forth. For enzyme systems addition of a substrate and/or a cofactor may be necessary.

In certain embodiments a second enzyme may be employed in addition to the enzyme of the enzyme conjugate. The enzymes of the pair of enzymes are related in that a product of the first enzyme serves as a substrate for the second enzyme.

The examination for presence and amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, actinometer, photographic instrument, and the like. The presence and amount of signal detected is related to the presence and amount of the amphetamine and/or methamphetamine analytes present in a sample above the predetermined cut-off level. Temperatures during measurements generally range from about 10° to about 70° C., more usually from about 20° to about 45° C., more usually about 20° to about 25° C. In one approach standard curves are formed using known concentrations of the analytes to be screened. As discussed above, calibrators and other controls may also be used.

Another aspect of the present invention relates to kits useful for conveniently performing an assay for the determination of amphetamine and/or methamphetamine analytes. In one embodiment a kit comprises in packaged combination an antibody for amphetamine, an antibody for methamphetamine, and a compound of Formula III wherein Z' is an enzyme. In another embodiment a kit of the invention comprises in packaged combination a conjugate of an enzyme and an amphetamine analog and/or a conjugate of an enzyme and a methamphetamine analog, an antibody for amphetamine raised against a compound of Formula III where $R^{1'}$ is H and $R^{2'}$ is H and Z' is an immunogenic carrier, and an antibody for methamphetamine raised against a compound of Formula III where $R^{1'}$ is H and $R^{2'}$ is $CH_3$ and Z' is an immunogenic carrier.

To enhance the versatility of the subject invention, the kit reagents can be provided in packaged combination, in the same or separate containers, in liquid or lyophilized form so that the ratio of the reagents provides for substantial optimization of the method and assay. The reagents may each be in separate containers or various reagents can be combined in one or more containers depending on the cross-reactivity and stability of the reagents.

The kit can further include other separately packaged reagents for conducting an assay such as additional sbp members, ancillary reagents such as an ancillary enzyme substrate, and so forth. The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

EXAMPLES

The invention is demonstrated further by the following illustrative examples. Parts and percentages recited herein are by weight unless otherwise specified. Temperatures are in degrees centigrade (° C.).

Analytical thin layer chromatography (TLC) was the usual analysis method and performed on Analtech Uniplate Silica Gel GF (0.25 mm) glass-backed plates using the specified solvent. The spots on TLC were visualized by ultraviolet light (short and/or long wave) and/or iodine vapors. Flash chromatography was carried out on Whatman silica gel 60 Å (230–400 mesh). All chemicals were obtained from Sigma Chemical Company (St. Louis, Mo.), Aldrich Chemical Company (St. Louis, Mo.), Fluka (Milwaukee Wis.) and Lancaster (Windham N.H.) and used as received. $^1$H-NMR and $^{13}$C-NMR spectra routinely recorded on a Bruker Ultrashiel™-400 (400 MHz) spectrometer (Bruker, Bellerica Mass.). Chemical shifts were reported in parts per million (ppm, δ) and related to tetramethylsilane or with deuterated solvent as internal reference. NMR abbreviations used are s (singlet), d (doublet), and m (multiplet). Mass spectra were obtained at the Mass Spectrometry Laboratory, University of California at Berkeley, Berkeley, Calif.

UV-visible absorption spectra were done on a HP 8452A diode array spectrophotometer. Fluorescence measurements were done on a Spex fluorolog spectrophotometer or a Perkin Elmer 650–40 spectrophotometer.

The following abbreviations have the meanings set forth below:
- g—grams
- mmol—millimolar
- DMF—dimethyl formamide
- THF—tetrahydrofuran
- NMR—nuclear magnetic resonance spectroscopy
- MHz—megahertz
- EDAC—-1-ethyl-3-(3-dimethylaminopropyl)carbodiimide hydrochloride (Sigma Chemical Company)
- MeOH—methanol
- EtOH—ethanol
- OAc—acetate
- AcOH—acetic acid
- FAB-MS—fast atom bombardment-mass spectrometry
- FAB-HRMS—fast atom bombardment—high resolution mass spectrometry
- EI-MS—electron impact mass spectroscopy
- EI—HRMS-electron impact high resolution mass spectroscopy
- DI water—deionized water
- TNBS—2,4,6-trinitrobenzesulfonic acid
- NHS—N-hydroxysuccinimic ester
- tBoc$_2$O—di-tert-butyldicarbonate
- TFA—trifluoroacetic acid
- MeI—methyl iodide Preparation of Metaraminol (12)

To a solution of [-]-m-hydroxyphenyl propanolamine bitartrate salt (11) (40 g, 126 mmol) in water (60 ml) was added slowly of NH$_4$OH (60 ml). The mixture was stirred at room temperature for 0.5 hour. The mixture was extracted with ethyl acetate (6×250 ml). The combined organic phase was washed with water (30 ml) and dried over anhydrous MgSO$_4$. The organic solvent was filtered and the filtrate was evaporated by rotary evaporation followed by high vacuum to dryness to give the desired product metaraminol (12) (16.8 g, 79.7% yield). This product was used for next reaction without further purification.

Preparation of Compound (13)

To a stirred solution of metaraminol (12) (16.8 g, 100.4 mmol) in chloroform (250 mL) was added slowly thionyl chloride (60 ml, 800 mmol) under argon. The reaction mixture was stirred for 0.5 hour and was heated at 50° C. for 45 minutes using an oil bath. The reaction mixture was cooled to room temperature. The chloroform and most of excess thionyl chloride were removed by rotary evaporation under high vacuum. After the evaporation, a crude solid residue was formed. The solid residue was dissolved in MeOH (250 ml) and heated with charcoal (30 g) at 70° C. by a water bath for 0.5 hour. The hot MeOH solution was filtered through a celite pad (0.5 cm thickness) on a filtering funnel. The filtrate was evaporated by rotary evaporation followed by high vacuum to dryness to give the desired product (13) (19.0 g, 85.5% yield). This product was used for the next reaction without further purification.

Preparation of Compound (14)

To a stirred solution of (13) (19.0 g, 85.54 mmol) in EtOH (100 ml) was added 10% Pd/C (7.0 g) and the solution was hydrogenated at a hydrogenator (parr) under 35 psi pressure of hydrogen for 16 hours. The ethanol solution was filtered through a celite pad (0.5 cm thickness) and the celite pad was washed with EtOH (30 ml). The combined filtrates were evaporated by rotary evaporation followed by high vacuum to dryness to give the desired product, (2S)-3-(2-aminopropyl)phenol hydrochloride (14) (16.1 g, 100% yield). $^1$H-NMR (CD$_3$OD, 400 MHz) δ: 7.15 (m, 1H), 6.90 (m, 3H), 3.48 (m, 1H), 2.85 (m, 1H), 2.70 (m, 1H), 1.24 (d, J=6.6 Hz, 3H). Optical rotation was +27.3 (c=1.0695); literature value +31.8 (c=2.0) This product was used for next reaction without further purification.

Preparation of Compound (15)

To a stirred solution of (14) (5 g, 26.64 mmol) in THF (150 ml) was added slowly triethylamine (3.8 ml, 27.2 mmol). The reaction mixture was stirred at room temperature for 10 minutes. Acetic anhydride (2.6 ml, 27.51 mmol) was added into the mixture followed by potassium carbonate (3.68 g, 26.63 mmol). The reaction mixture was stirred at room temperature for 3 hours. Water (50 ml) was added and most of THF was evaporated by rotary evaporation. The aqueous phase was extracted with ethyl acetate (4×120 ml). The combined organic phases were washed with water (40 mL) and dried over MgSO$_4$. The organic phase was evaporated to dryness by rotary evaporation and the residue was dissolved in methanol (40 ml) and NH$_4$OH (10 ml). The solution was stirred at room temperature for 0.5 hour and most of methanol was removed by rotary evaporation. Water (20 ml) was added and the aqueous phase was extracted with ethyl acetate (4×50 ml). The combined extracts were washed with water (15 ml) and dried over MgSO$_4$. The organic solvent was filtered and evaporated to dryness by rotary evaporation. The residue was purified by flash column chromatography (silica gel) using ethyl acetate/hexane (4/1) as an eluent to give acetamine (15) (3.90 g, 76% yield). $^1$H-NMR (CDCl$_3$, 400 MHz) δ:7.91 (m, 1H, OH), 7.12 (m, 1H), 6.77 (m, 2H), 6.68 (m, 1H), 5.61 (m, 1H, NH), 4.28 (s, 1H), 2.81 (m, 1H), 2.66 (m, 1H), 1.98 (s, 3H), 1.13 (d, J=6.5 Hz, 3H).

Preparation of Compound (16)

To a stirred solution of (15) (2.45 g, 12.68 mmol) in DMF (80 ml) was added NaH (0.5 g, 95%, 19.79 mmol) at 0° C. The reaction mixture was stirred at room temperature for 45 minutes under argon. After hydrogen evolution ceased, the reaction mixture was cooled to 0° C. and dimethylthiocarbamoyl chloride (2.35 g, 19.0 mmol) was added into the mixture. The reaction mixture was stirred and heated at 45° C. for 2 hours and allowed to cool to room temperature. Saturated sodium chloride solution (50 ml) and water (30 ml) were added to the mixture. The aqueous phase was extracted with ethyl acetate (3×100 ml) and the combined organic phase was washed with saturated NaCl solution (50 ml) and dried over MgSO$_4$. The organic solvent was filtered and evaporated to dryness by rotary evaporation. The residue was purified by flash column chromatography (silica gel) using ethyl acetate/hexane (9/1) as an eluent to give (16) (2.9 g, 81.6% yield). $^1$H-NMR (CDCl$_3$, 400 MHz) δ: 7.30 (m, 1H), 7.05 (m, 1H), 6.90 (m, 2H), 5.36 (m, 1H, NH), 4.30 (m, 1H), 3.44 (s, 3H), 3.34 (s, 3H), 2.79 (m, 2H), 1.93 (s, 3H), 1.09 (d, J=6.4 Hz, 3H).

Preparation of Compound (17)

Neat compound (16) (2.14 g, 7.60 mmol) was stirred and heated under argon at 238–243° C. in an oil bath for 8 hours. The complete reaction was observed by thin layer chromatography (TLC) (silica gel, ethyl acetate) by the disappearance of one spot and a new spot displayed on TLC. The reaction was allowed to cool to room temperature. The oily residue was purified by flash column chromatography (silica gel) using ethyl acetate as an eluent to give (17) (1.15 g, 53.7% yield). $^1$H-NMR (CDCl$_3$, 400 MHz) δ: 7.32–7.28 (m, 3H), 7.18 (m, 1H), 5.67 (m, 1H, NH), 4.25 (m, 1H), 3.08 (s, 3H), 3.00 (s, 3H), 2.78 (m, 2H), 1.93 (s, 3H), 1.05 (d, J=6.6 Hz, 3H); $^{13}$C-NMR (CDCl$_3$, 100 MHz) δ: 170.09, 167.31, 139.09, 137.27, 133.71, 130.76, 129.11, 128.92, 46.02, 42.14, 37.30, 23.62, 20.08.

Preparation of Compound (18)

A mixture of (17) (100 mg, 0.356 mmol) and KOH (400 mg, 7.13 mmol) in EtOH (9 ml) and water (6 ml) was refluxed under argon for 4 hours. Most of ethanol was evaporated and water (14 ml) was added to the mixture. The aqueous solution was acidified with 6N HCl (pH about 3) and then extracted with ethyl acetate (4×40 ml). The combined extracts were dried over MgSO$_4$, filtered, and evaporated to dryness by rotary evaporation. The residue was purified by flash column chromatography (silica gel) using ethyl acetate/hexane (9/1) as an eluent to give (18) (42 mg, 56.3% yield). FAB-MS: MH$^+$ (210); $^1$H-NMR (CDCl$_3$, 400 MHz) δ: 7.15–7.07 (m, 3H), 6.93 (m, 1H), 5.57 (m, 1H, NH), 4.20 (m, 1H), 3.42 (s, 1H, SH), 2.75 (m, 1H), 2.58 (m, 1H), 1.91 (s, 3H), 1.07 (d, J=6.6 Hz, 3H).

Preparation of Compound (19)

Compound (18) (206 mg, 0.984 mmol) in 3N HCl (30 ml) was refluxed under argon for 48 hours. The complete reaction was observed by thin layer chromatography (TLC) (silica gel, ethyl acetate/hexane=1/9). The reaction mixture was evaporated by rotary evaporation under high vacuum to dryness. The residues were dissolved in water (5 ml). The aqueous solution was frozen under argon and lyophilized to give (19) (192 mg, 95% yield). FAB-MS: MH$^+$ (168); $^1$H-NMR (D$_2$O, 400 MHz) δ: 7.29–7.08 (m, 3H), 6.95 (m, 1H), 3.40 (m, 1H), 2.76 (m, 2H), 1.06 (d, J=6.6 Hz, 3H); $^{13}$C-NMR (D$_2$O, 100 MHz) δ: 137.78, 132.10, 130.32, 130.00, 128.12, 127.11, 49.53, 40.30, 18.07.

Preparation of Compound (20)

To a stirred solution of (19) (192 mg, 0.942 mmol) in THF (12 ml) and water (6 ml) was added Di-tert-butyl-dicarbonate (420 mg, 1.92 mmol) at 0° C. The reaction mixture was stirred at room temperature for 2 hours under argon. Water (14 ml) was added to the mixture and most of THF was evaporated by rotary evaporation. The aqueous phase was extracted with ethyl acetate (3×70 ml) and the combined organic phase was washed with saturated NaCl solution (30 ml) and dried over MgSO$_4$. The organic solvent was filtered and evaporated to dryness. The residue was purified by flash column chromatography (silica gel) using ethyl acetate/hexane (1/4) as an eluent to give (20) (118 mg) and its disulfide dimer (20a) (98 mg). Both compounds have overall yield of 86%. (20a): FAB-MS: (MH$^+$, 533); $^1$H-NMR (CDCl$_3$, 400 MHz) δ: 7.34–7.18 (m, 6H), 7.04–7.02 (m, 2H), 4.34 (m, 2H, NH), 3.80 (m, 2H), 2.75 (m, 2H), 2.62 (m, 2H), 1.40 (s, 18H), 1.03 (d, J=6.6 Hz, 6H). (20): EI-MS m/z: 26 (M$^+$, 31), 211 (38), 194 (7), 151 (5), 144 (17), 123 (13), 88 (32), 57(100); $^1$H-NMR(CDCl$_3$, 400 MHz) δ: 7.15–7.08 (m, 3H), 6.95 (m, 1H), 4.38 (m, 1H, NH), 3.85 (m, 1H), 3.41(s, 1H, SH), 2.76 (m, 1H), 2.62 (m, 1H), 1.42 (s, 9H), 1.06 (d, J=6.6 Hz, 3H); $^{13}$C-NMR (CDCl$_3$, 100 MHz) δ: 155.56, 139.84, 131.07, 130.72, 129.43, 127.68, 127.26, 79.62, 47.79, 43.17, 28.87, 20.52.

Preparation of Monomer (20) from its Disulfide Dimer (20a)

To a stirred solution of dimer (20a) (138 mg, 0.259 mmol) in THF (8 ml) and NaOAc/AcOH buffer solution (5 ml, pH=5.0) was added Tris-(2-carboxyethyl) phosphine hydrochloride (TCEP) (76 mg, 0.265 mmol). The reaction mixture was stirred at room temperature for 0.5 hour under argon. Most of THF was evaporated by rotary evaporation and the aqueous phase was extracted with ethyl acetate (3×30 ml). The combined organic phase was washed with saturated NaCl solution (20 ml) and dried over MgSO$_4$. The organic solvent was filtered and evaporated to dryness. The residue was purified by flash column chromatography (silica gel) using ethyl acetate/hexane (1/4) as an eluent to give (20) (130 mg, 94% yield).

Preparation of Compound (21)

To a solution of (20) (10 mg, 0.0374 mmol) in ethyl acetate (2.5 ml) under argon was added slowly a solution of MeOH (7 μl) and acetyl bromide (12 μl) in ethyl acetate (0.5 ml). The reaction was stirred at 0° C. for 2 hours. The complete reaction was monitored by thin layer chromatography (TLC) (silica gel, ethyl acetate/hexane=1/4) by the disappearance of 20. The ethyl acetate was evaporated by rotary evaporation under high vacuum to dryness. The residues were dissolved in water (2 ml) and the aqueous phase was washed with ethyl acetate (0.5 ml). The aqueous solution was frozen under argon and lyophilized to give the desired hapten (21) (9 mg, 97% yield). FAB-MS: MH$^+$ (168); $^1$H-NMR (D$_2$O, 400 MHz) δ: 7.4–6.95 (m, 4H), 3.48 (m, 1H), 2.74 (m, 2H), 1.28 (d, J=6.3 Hz, 3H). $^{13}$C-NMR (D$_2$O, 100 MHz) δ: 137.53, 134.57, 131.49, 130.05, 129.66, 128.75, 49.29, 40.19, 17.76.

Preparation of Compound (22)

To a stirred solution of 1,3-dibromoacetone (144 mg, 0.667 mmol) in acetone (5 mL) at 0° C. under argon was added compound (20) (20 mg, 0.0748 mmol) and diisopropyl ethyl amine (14 μl, 0.08 mmol). The reaction mixture was stirred at 0° C. for 45 minutes under argon. Acetone was evaporated to dryness by rotary evaporation. The residue was purified by flash column chromatography (silica gel) using ethyl acetate/hexane (1/4) as an eluent to give (22) (20 mg, 66.5% yield). EI-MS m/z: 403(M$^+$, 52), 401 (M$^+$, 50), 347 (74), 345 (72), 330 (44), 328 (40), 260 (14), 258 (16), 144 (100), 88 (31), 57 (100); $^1$H-NMR(CDCl$_3$, 400 MHz) δ: 7.21–7.00 (m, 4H), 4.45 (m, 1H, NH), 4.07 (s, 2H), 3.87 (brs, 3H), 2.80 (m, 1H), 2.65 (m, 1H), 1.41 (s, 9H), 1.05 (d, J=6.4 Hz, 3H); $^{13}$C-NMR (CDCl$_3$, 100 MHz) δ: 197.05, 155.53, 140.06, 133.82, 131.69, 129.67, 129.26, 128.53, 79.62, 47.68, 43.09, 41.52, 32.47, 28.83, 20.47.

Preparation of Compound (23)

To a solution of (22) (20 mg, 0.0497 mmol) in CH$_2$Cl$_2$ (2 ml) was added trifluoroacetic acid (0.2 ml, 2.6 mmol). The reaction was stirred at room temperature for 0.5 hour. The excess of trifluoroacetic acid and the solvent CH$_2$Cl$_2$ were removed by rotary evaporation and put in high vacuum. This gave the desired product (23) (20 mg, 96.7% yield). ES-MS: Calcd for C$_{12}$H$_{17}$BrNOS: 304 ($^{81}$Br), 302($^{79}$Br); Found: 304, 302; FAB-MS: 304, 302; FAB-HRMS Calcd for C$_{12}$H$_{17}$BrNOS: 304.0194($^{81}$Br), 302.0214($^{79}$Br); Found: 304.0198, 302.0209; $^1$H-NMR(CDCl$_3$, 400 MHz) δ: 7.81 (m, NH), 7.23–7.06 (m, 4H), 4.07 (s, 2H), 3.87 (s, 2H), 3.52 (m, 1H), 2.80 (m, 1H), 1.30 (brs, 3H); $^{13}$C-NMR (CDCl$_3$, 100 MHz) δ: 197.5, 137.3, 134.6, 131.2, 130.3, 129.5, 128.9, 50.1, 41.2, 40.9, 32.6, 18.5.

Preparation of Compound (26)

To a stirred solution of (14) (271 mg, 1.44 mmol) in CH$_2$Cl$_2$ (30 ml) was added KHCO$_3$ (144 mg, 1.44 mmol) followed by adding slowly triethylamine (0.8 ml, 5.73 mmol). The reaction mixture was stirred at room temperature for 20 minutes. Trifluoroacetic anhydride (0.6 ml, 4.24 mmol) was added into the mixture. The reaction mixture was stirred at room temperature for 4 hours. Water (15 ml) was added and the organic phase was separated. The aqueous phase was extracted with $CH_2Cl_2$ (4×30 ml). The combined organic phase were washed with 10% $NaHCO_3$ solution (30 mL) and dried over $MgSO_4$. The organic phase was filtered and evaporated to dryness by rotary evaporation. The residue was purified by flash column chromatography (silica gel) using ethyl acetate/hexane (2/3) as an eluent to give (26) (274 mg, 77% yield). FAB-MS:$MH^+$ (248,100%); $^1$H-NMR ($CDCl_3$, 400 MHz) δ: 7.17–7.14 (m, 1H), 6.74–6.64 (m, 3H), 6.34 (m, 1H, NH), 5.91 (m, 1H, OH), 4.25 (m, 1H), 2.80–2.73 (m, 2H), 1.20 (d, J=5.9 Hz, 3H). This reaction was repeated by using 10.9 g of (14) and 8.6 g of (26) was obtained.

Preparation of Compound (27)

To a stirred solution of (26) (1.65 g, 6.67 mmol) in DMF (30 ml) under argon was added NaH (332 mg, 95%, 13.14 mmol) at 0° C. The reaction mixture was stirred at 0° C. for 10 minutes and at room temperature for 45 minutes. After hydrogen evolution ceased, the reaction mixture was cooled to 0° C. and dimethylthiocarbamoyl chloride (1.23 g, 9.95 mmol) was added. The reaction mixture was stirred and heated at 40° C. for 2 hours and allowed to cool to room temperature. Saturated sodium chloride solution (15 ml) and water (35 ml) was added to the mixture. The aqueous phase was extracted with ethyl acetate (4×80 ml) and the combined organic phase were washed with saturated NaCl solution (50 ml) and dried over $MgSO_4$. The organic solvent was filtered and evaporated to dryness by rotary evaporation. The residue was purified by flash column chromatography (silica gel) using ethyl acetate/hexane (3/7) as an eluent to give (27) (1.12 g, 68% yield). $^1$H-NMR ($CDC_3$, 400 MHz) δ: 7.25 (m, 1H), 7.00 (m, 2H), 6.90 (m, 1H), 6.81 (m, 1H, NH), 4.20 (m, 1H), 3.36 (s, 3H), 3.24 (s, 3H), 2.85 (m, 1H), 2.72 (m, 1H), 1.15 (d, J=6.7 Hz, 3H); $^{13}$C-NMR ($CDCl_3$, 100 MHz) δ: 187.93, 157.06, 154.51, 138.89, 129.60, 127.17, 124.19, 121.48. 47.91, 43.54, 41.79, 39.07, 19.56. HRFAB-MS Calcd for $C_{14}H_{18}F_3N_2O_2S$: 335.1042; Found: 335.1041.

Preparation of Compound (28)

Neat compound (27) (1.0 g, 2.99 mmol) was stirred and heated under argon at 238-243° C. in an oil bath for 9 hours. The complete reaction was observed by thin layer chromatography (TLC) (silica gel, ethyl acetate/hexane=3/7) by the disappearance of (27) and a new spot displayed at TLC which is more polar than (27). The reaction was allowed to cool to room temperature. The oily residue was purified by flash column chromatography (silica gel) using ethyl acetate/hexane=3/7 as an eluent to give (28) (0.702 g, 70% yield). $^1$H-NMR ($CDCl_3$, 400 MHz) δ: 7.35–7.27 (m, 3H), 7.13 (m, 1H), 6.75 (m, 1H, NH), 4.22 (m, 1H), 3.07 (s, 3H), 2.98 (s, 3H), 2.80–2.72 (m, 2H), 1.11 (d, J=6.7 Hz, 3H); $^{13}$C-NMR ($CDCl_3$, 100 MHz) δ: 167.35, 156.8, 138.11, 137.16, 134.40, 130.67, 129.41, 128.92, 47.49, 41.56, 37.33, 19.57; HRFAB-MS Calcd for $C_{14}H_{18}F_3N_2O_2S$: 335.1042; Found: 335.1041.

Preparation of Compound (30)

A mixture of (28) (650 mg, 1.944 mmol) and KOH (1.63 g, 29 mmol) in EtOH (30 ml) and water (20 ml) was refluxed under argon for 6 hours. The reaction mixture was allowed to cool down to room temperature. The aqueous solution was acidified with 1N HCl (pH about 3). Most of ethanol was evaporated by rotary evaporation. The aqueous was frozen in dry ice and lyophilized to give hydrochloride salt of (29). $^1$H-NMR ($D_2O$, 400 MHz) δ: 7.30–7.00 (m, 4H), 3.52 (m, 1H), 2.84 (m, 2H), 1.24 (d, J=6.6 Hz, 3H).

To a stirred solution of (29) in THF (24 ml) and water (8 ml) was added di-tert-butyl-dicarbonate (850 mg, 3.89 mmol) and $K_2CO_3$ (553 mg, 4.0 mmol) at 0° C. The reaction mixture was stirred at room temperature for 2 hours under argon. Water (20 ml) was added to the mixture and most of THF was evaporated by rotary evaporation. The aqueous phase was extracted with ethyl acetate (3×80 ml) and the combined organic phase was washed with saturated NaCl solution (40 ml) and dried over $MgSO_4$. The organic solvent was filtered and evaporated to dryness. The residue was purified by flash column chromatography (silica gel) using ethyl acetate/hexane (1/4) as an eluent to give 30 (352 mg, 68%). $^1$H-NMR of (30) is identical with that of (20) indicating that both compounds (30) and (20) are the same compound.

Preparation of Compound (31)

To a solution of divinyl sulfone (0.075 ml, 0.748 mmol) in anhydrous THF (5 ml) was added NaH (3.0 mg, 0.119 mmol) followed by the addition of (30) (20 mg, 0.0748 mmol) at 0° C. under argon. The reaction mixture was stirred at 0° C. under argon for 45 minutes. Water (0.1 ml) was added and THF was removed by rotary evaporation. The residue was put in high vacuum line to remove trace of water. The oily residue was purified by flash column chromatography (silica gel) by using ethyl acetate/hexane=1/4, 100 ml) followed by acetate/hexane=1/1 as an eluent to give (31) (26 mg, 90% yield). $^1$H-NMR($CDCl_3$, 400 MHz) δ: 7.23–7.04 (m, 4H), 6.65 (dd, J=9.8, 16.6 Hz, 1H), 6.43 (d, J=16.6 Hz, 1H), 6.18 (d, J=9.8 Hz, 1H), 4.40 (m, 1H, NH), 3.83 (m, 1H), 3.20 (s, 4H), 2.74 (m, 1H), 2.63 (m, 1H), 1.38 (s, 9H), 1.07 (d, J=6.7 Hz, 3H); $^{13}$C-NMR ($CDCl_3$, 100 MHz) δ: 155.51, 140.29, 136.41, 133.68, 131.85, 131.68, 129.68, 129.05, 128.78, 54.22, 47.87, 43.36, 28.80, 26.63, 20.67.

Preparation of Compound (32)

To a solution of (31) (23 mg, 0.0597 mmol) in $CH_2Cl_2$ (3 ml) was added trifluoroacetic acid (0.3 ml, 3.92 mmol). The reaction was stirred at room temperature for 30 minutes. Excess trifluoroacetic acid and excess solvent $CH_2Cl_2$ were removed by rotary evaporation and the residue was subjected to high vacuum. This gave the desired product (32) (23 mg, 97% yield). FAB-MS: $MH^+$ (286); $^1$H-NMR ($CDCl_3$, 400 MHz) δ: 7.70 (m, NH), 7.27–7.04 (m, 4H), 6.61 (dd, J=9.8, 16.6 Hz, 1H), 6.40 (d, J=16.5 Hz, 1H), 6.19 (d, J=9.8 Hz, 1H), 3.52 (m, 1H), 3.19 (s, 4H), 3.00 (m, 1H), 2.79 (m, 1H), 1.28 (d, J=6.4 Hz, 3H); $^{13}$C-NMR ($CDCl_3$, 100 MHz) δ: 137.43, 135.93, 134.79, 132.18, 131.18, 130.33, 129.84, 128.67, 54.08, 49.98, 40.94, 26.35, 18.45; FAB-HRMS Calcd for $C_{13}H_{20}NO_2S_2$: 286.0935; Found: 286.0935.

Preparation of Compound (33)

To a stirred solution of (28) (678 mg, 2.01 mmol) in THF (60 ml) under argon was added KH (231 mg, 5.75 mmol, freed from protective mineral oil by washing with hexane three times followed by centrifugation). The reaction mixture was stirred for 10 minutes and 18-crown-6 (230 mg) and MeI (2.0 mL, 32 mmol) was added to the mixture. The reaction mixture was allowed to stir at room temperature for 2 hours and refluxed for 16 hours. Most of THF was removed by rotary evaporation and ethyl acetate (60 ml) was added to the mixture followed by cautiously adding of 10% aqueous HCl (10 ml) and water (20 ml). The organic phase was separated and the aqueous phase was extracted with ethyl acetate (3×50 ml) and the combined organic phase were washed with water (30 ml) and dried over $MgSO_4$. The organic solvent was filtered and evaporated to dryness by rotary evaporation. The residue was purified by flash column chromatography (silica gel) using ethyl acetate/hexane (3/7) as an eluent to give (33) (490 mg, 70% yield). $^1$H-NMR ($CDCl_3$, 400 MHz) δ: 7.36–7.19 (m, 4H), 4.75, 4.20 (m, 1H), 3.08 (s, 3H), 2.98 (s, 3H), 2.90, 2.93 (s, 3H), 2.87–2.75 (m, 2H), 1.22 (m, 3H); $^{13}$C-NMR (CDCl$_3$, 100 MHz) δ: 167.20, 157.12, 138.60, 138.20, 136.65, 134.65, 134.41, 130.12, 129.63, 124.19, 54.58, 53.12, 41.17, 39.54, 37.33, 29.81, 28.46, 18.30, 16.98; HRFAB-MS Calcd for C$_{15}$H$_{20}$F$_3$N$_2$O$_2$S: 349.1198; Found: 349.1194.

Preparation of Compound (34)

A mixture of (33) (457 mg, 1.31 mmol) and KOH (1.1 g, 19.6 mmol) in EtOH (24 ml) and water (16 ml) was refluxed under argon for 6 hours. The reaction mixture was allowed to cool to room temperature. The aqueous solution was acidified with 1N HCl (pH about 3). Most of ethanol was evaporated by rotary evaporation. The aqueous phase was frozen in dry ice and lyophilized to give hydrochloride salt of (34). $^1$H-NMR (D$_2$O, 400 MHz) δ: 7.40–7.00 (m, 4H), 3.40 (m, 1H), 2.93 (m, 1H), 2.72 (m, 1H), 2.62 (s, 3H), 1.17 (d, J=6.5 Hz, 3H).

Preparation of Compound (35)

To a stirred solution of (34) in THF (18 ml) and water (6 ml) was added di-tert-butyl-dicarbonate (571 mg, 2.62 mmol) and K$_2$CO$_3$ (387 mg, 2.80 mmol) at 0° C. The reaction mixture was stirred at room temperature for 2 hours under argon. Water (15 ml) was added to the mixture and most of THF was evaporated by rotary evaporation. The aqueous phase was extracted with ethyl acetate (3×70 ml) and the combined organic phase was washed with saturated NaCl solution (35 ml) and dried over MgSO$_4$. The organic solvent was filtered and evaporated to dryness. The residue was purified by flash column chromatography (silica gel) using ethyl acetate/hexane (15/85) as an eluent to give (35) (295 mg, 80%) and its disulfide dimer (35a) (40 mg, 11.4%). (35): FAB-MS:(MH$^-$, 282); $^1$H-NMR (CDCl$_3$, 400 MHz) δ: 7.20–6.80 (m, 4H), 4.46–4.32 (m, 1H), 3.39 (s, 1H, SH), 2.73–2.50 (m, 5H), 1.37–1.30 (m, 9H) 1.12 (m, 3H); $^{13}$C-NMR (CDCl$_3$, 100 MHz) δ: 155.87, 147.14, 140.45, 133.03, 130.93, 130.30, 129.37 127.67, 126.83, 85.59, 79.61, 52.81, 51.44, 40.77, 28.75, 28.59, 27.82, 18.89, 17.96.

Preparation of Compound (36)

To a solution of (35) (13 mg, 0.0462 mmol) in ethyl acetate (4.5 ml) under argon was added slowly a solution of MeOH (80 μl) and acetyl bromide (100 μl) in ethyl acetate (0.5 ml). The reaction was stirred at 0° C. for 1 hour and at room temperature for half hour. The complete reaction was monitored by thin layer chromatography (TLC) (silica gel, ethyl acetate/hexane=1/4). The ethyl acetate was evaporated by rotary evaporation under high vacuum to dryness. The residues were dissolved in water (0.5 ml). The aqueous solution was frozen under argon and lyophilized to give the desired hapten (36) (12 mg, 99% yield). FAB-MS: (MH$^+$, 182); $^1$H-NMR (D$_2$O, 400 MHz) δ: 7.32–6.93 (m, 4H), 3.35 (m, 1H), 2.85 (m, 2H), 2.67 (m, 2H), 2.54 (s, 3H), 1.09 (d, J=6.6 Hz, 3H); $^{13}$C-NMR (D$_2$O, 100 MHz) δ: 137.21, 132.08, 130.10, 129.78, 128.00, 126.86, 56.58, 38.80, 30.27, 15.15.

Preparation of Compound (37)

To a stirred solution of 1,3-dibromoacetone (263 mg, 0.667 mmol) in acetone (8 mL) at 0° C. under argon was added compound (35) (38 mg, 0.135 mmol) and diisopropyl ethyl amine (26 μl, 0.149 mmol). The reaction mixture was stirred at 0° C. for 45 minutes under argon. Acetone was evaporated to dryness by rotary evaporation. The residue was purified by flash column chromatography (silica gel) using ethyl acetate/hexane (1/4) as an eluent to give (37) (24 mg, 43% yield) $^1$H-NMR(CDCl$_3$, 400 MHz) δ: 7.20–7.01 (m, 4H), 4.48–4.26 (m, 1H), 4.07 (s, 2H), 3.87 (s, 2H), 2.72–2.60 (m, 5H), 1.40–1.29 (m, 9H), 1.20 (m, 3H); $^{13}$C-NMR (CDCl$_3$, 100 MHz) δ: 197.19, 155.86, 140.97, 133.30, 130.91, 129.64, 128.60, 128.13, 79.63, 52.89, 51.46, 41.55, 40.74, 32.60, 28.77, 28.01, 18.85, 18.05; HREI-MS Calcd for C$_{18}$H$_{26}$BrNO$_3$S: 415.0816; Found: 415.0810.

Preparation of Compound (38)

To a solution of (37) (8 mg, 0.0192 mmol) in CH$_2$Cl$_2$ (2 ml) was added trifluoroacetic acid (0.1 ml, 1.3 mmol). The reaction was stirred at 0° C. for 15 minutes and at room temperature for 20 minutes. Excess trifluoroacetic acid and excess solvent CH$_2$Cl$_2$ were removed by rotary evaporation and the residue was subjected to high vacuum. This gave the desired product (38) (9 mg, 98% yield). $^1$H-NMR(CDCl$_3$, 400 MHz) δ: 9.10–8.93 (m, NH), 7.25–7.04 (m, 4H), 4.09 (s, 2H), 3.89 (s, 2H), 3.34 (m, 1H), 3.19 (m, 1H), 2.77 (m, 1H), 2.69 (s, 3H), 1.29 (d, J=6.5 Hz, 3H); $^{13}$C-NMR (CDCl$_3$, 100 MHz) δ: 197.02, 137.09, 134.88, 131.05, 130.33, 129.52, 128.81, 57.31, 41.12, 39.72, 32.47, 30.90, 15.78. FAB-HRMS Calcd for C$_{13}$H$_{19}$BrNOS: 316.0370($^{79}$Br), 318.0350 ($^{81}$Br); Found: 316.0373, 318.0351.

Preparation of Compound (39)

To a solution of divinyl sulfone (0.178 ml, 1.77 mmol) in anhydrous THF (6 ml) was added NaH (8.0 mg, 0.316 mmol) followed by addition of (35) (50 mg, 0.177 mmol) at 0° C. under argon. The reaction mixture was stirred at 0° C. under argon for 45 minutes. Water (0.1 ml) was added and THF was removed by rotary evaporation. The residue was put in high vacuum line to remove trace of water. The oily residue was purified by flash column chromatography (silica gel) using ethyl acetate/hexane=1/4 (100 ml) followed by acetate/hexane=1/1 as an eluent to give (39) (51 mg, 72% yield). $^1$H-NMR(CDCl$_3$, 400 MHz) □δ: 7.20–7.03 (m, 4H), 6.70 (dd, J=9.9, 16.5 Hz, 1H), 6.43 (d, J=16.5 Hz, 1H), 6.17 (d, J=9.9 Hz, 1H), 4.49–4.29 (m, 1H), 3.20 (m, 4H), 2.71–2.64 (m, 5H), 1.32–1.26 (m, 9H), 1.13 (m, 3H); $^{13}$C-NMR (CDCl$_3$, 100 MHz) δ: 155.82, 141.07, 137.28, 136.52, 133.72, 131.53, 130.30, 129.70, 128.57, 79.57, 54.22, 52.86, 51.50, 40.74, 28.73, 26.45, 19.00, 18.15.

Preparation of Compound (40)

To a solution of (39) (22 mg, 0.055 mmol) in CH$_2$Cl$_2$ (3 ml) was added trifluoroacetic acid (0.3 ml, 3.92 mmol). The reaction was stirred at room temperature for 30 minutes. Excess trifluoroacetic acid and excess solvent CH$_2$C$_2$ were removed by rotary evaporation and the residue was subjected to high vacuum. This gave the desired product (40) (22.5 mg, 98% yield). FAB-MS: (MH$^+$, 300); $^1$H-NMR (CDCl$_3$, 400 MHz) □δ: 8.90 (m, NH), 7.28–7.04 (m, 4H), 6.63 (dd, J=9.8, 16.5 Hz, 1H), 6.43 (d, J=16.5 Hz, 1H), 6.20 (d, J=9.8 Hz, 1H), 3.38 (m, 1H), 3.20 (m, 5H), 2.78–2.70 (m, 4H), 1.26 (d, J=6.3 Hz, 3H); $^{13}$C-NMR (CDCl$_3$, 100 MHz) δ: 137.29, 136.15, 134.99, 132.00; 131.02, 130.32, 129.55, 128.62, 57.08, 54.10, 39.69, 30.83, 26.27, 15.71; FAB-HRMS Calcd for C$_{14}$H$_{22}$NO$_2$S$_2$: 300.1093; Found: 300.1096.

Preparation of Antibodies

The antibodies used in some of the experiments herein are monoclonal antibodies prepared as described in U.S. Pat. Nos. 5,328,828 and 5,135,863, the relevant disclosures of which have been incorporated hereinabove by reference. In particular, see, for example, column 37, line 16, to column 39, line 55, of U.S. Pat. No. 5,135,863.

In general, the monoclonal antibodies are produced according to the standard techniques of Köhler and Milstein, *Nature* 265:495–497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3–46 (1981). Samples of an appropriate immunogen preparation are injected into an animal such as a mouse and, after a sufficient time, the animal is sacrificed and spleen cells obtained. Alternatively, the spleen cells of a non-immunized animal can be sensitized to the immunogen in vitro. The spleen cell chromosomes encoding the base sequences for the desired immunoglobulins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Köhler and Milstein, supra).

Polyclonal antibodies are produced by procedures as discussed below using immunogenic conjugates of compounds 21 and 23, respectively. Antiserum containing antibodies is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7: 1–24 (1975); Broughton and Strong, Clin. Chem. 22: 726–732 (1976); and Playfair, et al., Br. Med. Bull. 30: 24–31 (1974).

Preparation of Enzyme Conjugates Using Compounds (21), (23), (32), (36), (38) and (40) Respectively Compounds (23), (32), (38) and (40), prepared as described above, are allowed to react with a glucose-6-phosphate dehydrogenase (G6PDH) mutant enzyme to form the respective enzyme conjugates (25), (41), (43), and (44). In this mutant enzyme, one amino acid in the primary amino acid sequence has been replaced with a cysteine. The mutant enzyme is obtained by the procedure disclosed in U.S. Pat. Nos. 6,090,567 and 6,033,890, the relevant disclosures of which were incorporated hereinabove by reference. Compounds (21) and (36), prepared as described above, are allowed to react with a modified bromoacetyl-glucose-6-phosphate dehydrogenase (G6PDH) wide type enzyme to form the respective enzyme conjugates (24) and (42). The conjugation technique disclosed in U.S. Pat. Nos. 6,090,567 and 6,033,890 is then utilized to couple the compound (21), (23), (32), (36), (38) or (40) respectively, to the enzyme through a thioether linkage. The preparation is similar to that described in U.S. Pat. No. 6,090,567 in particular at column 28, line 44, to column 43, line 29, the disclosure of which is incorporated herein by reference.

Inhibition of the G6PDH Conjugates by Amphetamine or Methamphetamine Antibody

For a conjugate to have utility in EMIT assays, the antibody must inhibit the conjugate. Therefore, the selected conjugates (24), (25) and (42) are incubated in the presence of respective antibodies for amphetamine (Conjugates (24) and (25)) or methamphatemine (Conjugate (42)) and tested for activity. The conditions and duration of incubation for conjugates (25) and (42) were as follows: An appropriate dilution of conjugate was mixed with amphetamine antibody (Conjugate (25)) or methamphetamine antibody (Conjugate (42)) deionized water and glucose-6-phosphate dehydrogenous substrates at an appropriate pH and ionic strength, in a total volume of 318 µL. After a 100-sec incubation at 37° C., the enzyme activity ($\Delta A$/min at 340 nm) was measured. Control experiments with deionized water instead of antibody established the uninhibited baseline activity, which was compared to the activity in the presence of antibody to establish the degree of antibody dependent conjugate inhibition. The conditions and duration of incubation for conjugate (24) were as follows: An appropriate dilution of conjugate was mixed with amphetamine antibody, and glucose-6-phosphate dehydrogenase substrates at an appropriate ionic strength and pH in a final volume of 900 µL. After a 15-sec incubation at 30° C., the enzyme activity (($\Delta A$/0.5 min at 340 nm) was measured. Control experiments with buffer instead of antibody established the uninhibited baseline activity, which was compared to the activity in the presence of antibody to establish the degree of antibody dependent conjugate inhibition (Notebook S4768:89). The results show that there is an antibody dependent inhibition of the conjugate.

Assay for Amphetamine and Methamphetamine

The enzyme conjugates (24) or (25) are employed along with appropriate antibody reagents and ancillary reagents to detect the presence of amphetamine or methamphetamine in a sample.

The above discussion includes certain theories as to mechanisms involved in the present invention. These theories should not be construed to limit the present invention in any way, since it has been demonstrated that the present invention achieves the results described.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A compound of the formula:

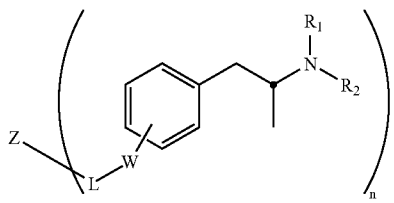

wherein:
- $R^1$ is H, lower alkyl, a protecting group,
- $R^2$ is H, lower alkyl, a protecting group,
- L is —$(CH_2)_t$—X—$(CH_2)_v$—Y— wherein X is C(O) or $SO_2$, Y is a bond, S or —$NR^3$ wherein $R^3$ is H or lower alkyl, W is O, S, or NH, and t is an integer from 1 to 6 and v is an integer from 2 to 6,
- Z is H, a protecting group, a poly(amino acid), a non-poly(amino acid) label moiety, a non-poly(amino acid) immunogenic carrier, or a functional group excluding thiol,
- n is 1 when Z is other than a poly(amino acid) or, when Z is a poly(amino acid), n is an integer between 1 and the molecular weight of the poly(amino acid) divided by 500;

and salts thereof.

2. A compound according to claim 1 wherein $R^1$ is H and $R^2$ is H.

3. A compound according to claim 1 wherein $R^1$ is H and $R^2$ is lower alkyl.

4. A compound according to claim 3 wherein lower alkyl is methyl.

5. A compound according to claim 1 wherein Z is a poly(amino acid).

6. A compound according to claim 5 wherein said poly(amino acid) is an enzyme or a protein immunogenic carrier.

7. A compound of the formula:

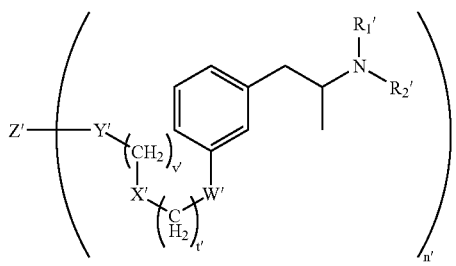

wherein:
- $R^{1\prime}$ is H, lower alkyl, a protecting group,
- $R^{2\prime}$ is H, alkyl, a protecting group,
- W' is O, S or $NR^3$ wherein $R^3$ is H or lower alkyl,
- X' is C(O) or $SO_2$,
- Y' is bond, S or —$NR^3$ wherein $R^3$ is H or lower alkyl,
- Z' is H, a protecting group, a poly(amino acid), a non-poly(amino acid) label moiety, a non-poly(amino acid) immunogenic carrier, or a functional group,
- t' is an integer from 1 to 6 and v' is an integer from 2 to 6,
- n' is 1 when Z' is other than a poly(amino acid) or, when Z' is a poly(amino acid), n' is an integer between 1 and the molecular weight of the poly(amino acid) divided by 500;

and salts thereof.

8. A compound according to claim 7 wherein $R^{1\prime}$ is H and $R^{2\prime}$ is H.

9. A compound according to claim 7 wherein $R^{1\prime}$ is H and $R^{2\prime}$ is methyl.

10. A compound according to claim 7 wherein Z' is a poly(amino acid).

11. A compound according to claim 7, wherein said stereoisomeric mixture comprises at least 90% of one stereoisomeric form over the other.

12. A compound according to claim 11 wherein said stereoisomer has the formula:

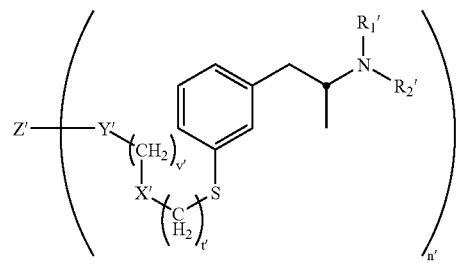

13. A compound of the formula:

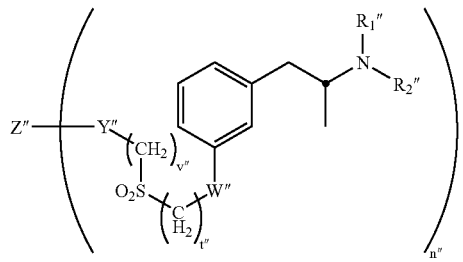

wherein:
- $R^{1\prime\prime}$ is H, lower alkyl, a protecting group,
- $R^{2\prime\prime}$ is H, lower alkyl, a protecting group,
- W" is O, S, or $NR^{3\prime}$ wherein $R^{3\prime}$ is H or lower alkyl,
- Y" is bond, S or —$NR^{3\prime}$ wherein $R^{3\prime}$ is H or lower alkyl,
- Z" is H, a protecting group, a poly(amino acid), a non-poly(amino acid) label moiety, a non-poly(amino acid) immunogenic carrier, or a functional group,
- t" is an integer from 1 to 6 and v" is an integer from 2 to 6,
- n" is 1 when Z" is other than a poly(amino acid) or, when Z" is a poly(amino acid), n" is an integer between 1 and the molecular weight of the poly(amino acid) divided by 500;

and salts thereof.

14. A compound according to claim 13 wherein $R^{1\prime\prime}$ is H and $R^{2\prime\prime}$ is H.

15. A compound according to claim 13 wherein $R^{1\prime\prime}$ is H and $R^{2\prime\prime}$ is methyl.

16. A compound according to claim 13 wherein Z" is an enzyme.

17. A compound according to claim 16 wherein said enzyme is glucose-6-phosphate dehydrogenase.

18. A compound according to claim 13 wherein Z" is a protein immunogenic carrier or a non-poly(amino acid) immunogenic carrier.

19. An antibody raised against a compound according to claim 18.

20. A reagent system comprising a compound according to claim 16, an antibody for amphetamine and/or an antibody for methamphetamine.

21. A reagent system comprising an antibody according to claim 19 and an enzyme conjugate of an amphetamine and/or an enzyme conjugate of methamphetamine.

22. A compound of the formula:

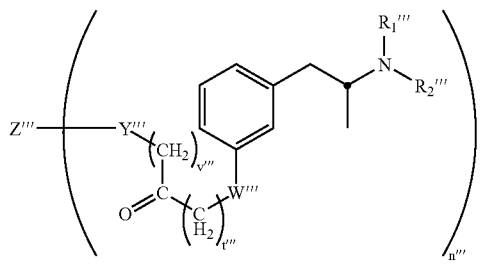

wherein:
R$^{1'''}$ is H, lower alkyl, a protecting group,
R$^{2'''}$ is H, lower alkyl, a protecting group,
W''' is O, S, or NR$^{3'''}$ wherein R$^{3'''}$ is H or lower alkyl,
Y''' is a bond, S or —NR$^{3'''}$ wherein R$^{3'''}$ is H or lower alkyl,
Z''' is H, a protecting group, a poly(amino acid), a non-poly(amino acid) label moiety, a non-poly(amino acid) immunogenic carrier, or a functional group,
t''' is an integer from 1 to 6 and v''' is an integer from 2 to 6,
n''' is 1 when Z''' is other than a poly(amino acid) or, when Z''' is a poly(amino acid), n''' is an integer between 1 and the molecular weight of the poly(amino acid) divided by 500;
and salts thereof.

23. A compound according to claim 22 wherein R$^{1'''}$ is H and R$^{2'''}$ is H.

24. A compound according to claim 22 wherein R$^{1'''}$ is H and R$^{2'''}$ is methyl.

25. A compound according to claim 22 wherein Z''' is an enzyme.

26. A compound according to claim 25 wherein said enzyme is glucose-6-phosphate dehydrogenase.

27. A compound according to claim 22 wherein Z''' is an antigen or a non-poly(amino acid) immunogenic carrier.

28. An antibody raised against a compound according to claim 27.

29. A reagent system comprising a compound according to claim 25, an antibody for amphetamine and/or an antibody for methamphetamine.

30. A reagent system comprising an antibody according to claim 28 and an enzyme conjugate of an amphetamine and/or an enzyme conjugate of methamphetamine.

31. A method for determining amphetamine and/or methamphetamine in a sample suspected of containing amphetamine and/or methamphetamine, said method comprising:
(a) providing in combination in a medium:
(i) said sample and
(ii) a reagent system according to claim 20; and
(b) examining said medium for the presence of a complex comprising said amphetamine and said antibody for amphetamine and/or a complex of said methamphetamine and said antibody for methamphetamine, the presence thereof indicating the presence of said amphetamine and/or methamphetamine in said sample.

32. A method according to claim 31 wherein said examining comprises measuring signal from said enzyme, the amount thereof being related to the presence of said amphetamine and/or methamphetamine in said sample.

33. A method according to claim 32 wherein said method is a homogeneous method and said medium is examined for the amount of said signal.

34. A method according to claim 32 wherein said method is a heterogeneous method and said complex, if present, is separated from said medium and said medium or said complex is examined for the amount of said signal.

35. A method for determining amphetamine and/or methamphetamine in a sample suspected of containing amphetamine and/or methamphetamine, said method comprising:
(a) providing in combination in a medium:
(i) said sample and
(ii) a reagent system according to claim 21; and
(b) examining said medium for the presence of a complex comprising said amphetamine and said antibody for amphetamine and/or a complex of said methamphetamine and said antibody for methamphetamine, the presence thereof indicating the presence of said amphetamine and/or methamphetamine in said sample.

36. A method according to claim 35 wherein said examining comprises measuring signal from said enzyme, the amount thereof being related to the presence of said amphetamine and/or methamphetamine in said sample.

37. A method according to claim 36 wherein said method is a homogeneous method and said medium is examined for the amount of said signal.

38. A method according to claim 36 wherein said method is a heterogeneous method and said complex, if present, is separated from said medium and said medium or said complex is examined for the amount of said signal.

39. A method for determining amphetamine and/or methamphetamine in a sample suspected of containing amphetamine and/or methamphetamine, said method comprising:
(a) providing in combination in a medium:
(i) said sample and
(ii) a reagent system according to claim 29; and
(b) examining said medium for the presence of a complex comprising said amphetamine and said antibody for amphetamine and/or a complex of said methamphetamine and said antibody for methamphetamine, the presence thereof indicating the presence of said amphetamine and/or methamphetamine in said sample.

40. A method according to claim 39 wherein said examining comprises measuring signal from said enzyme, the amount thereof being related to the presence of said amphetamine and/or methamphetamine in said sample.

41. A method according to claim 40 wherein said method is a homogeneous method and said medium is examined for the amount of said signal.

42. A method according to claim 40 wherein said method is a heterogeneous method and said complex, if present, is separated from said medium and said medium or said complex is examined for the amount of said signal.

43. A method for determining amphetamine and/or methamphetamine in a sample suspected of containing amphetamine and/or methamphetamine, said method comprising:

(a) providing in combination in a medium:
  (i) said sample and
  (ii) a reagent system according to claim 30; and
(b) examining said medium for the presence of a complex comprising said amphetamine and said antibody for amphetamine and/or a complex of said methamphetamine and said antibody for methamphetamine, the presence thereof indicating the presence of said amphetamine and/or methamphetamine in said sample.

44. A method according to claim 43 wherein said examining comprises measuring signal from said enzyme, the amount thereof being related to the presence of said amphetamine and/or methamphetamine in said sample.

45. A method according to claim 44 wherein said method is a homogeneous method and said medium is examined for the amount of said signal.

46. A method according to claim 44 wherein said method is a heterogeneous method and said complex, if present, is separated from said medium and said medium or said complex is examined for the amount of said signal.

47. A method for determining amphetamine and/or methamphetamine in a sample suspected of containing amphetamine and/or methamphetamine, said method comprising:
(a) providing in combination in a medium:
  (i) said sample,
  (ii) an antibody for amphetamine,
  (iii) an antibody for methamphetamine,
  (iv) a compound of the formula:

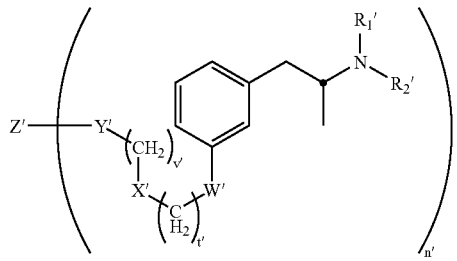

wherein:
  $R^{1\prime}$ is H, lower alkyl, a protecting group,
  $R^{2\prime}$ is H, lower alkyl, a protecting group,
  W' is O, S, or $NR^{3\prime}$ wherein $R^{3\prime}$ is H or lower alkyl,
  X' is C(O) or $SO_2$,
  Y' is bond, S or —$NR^{3\prime}$ wherein $R^{3\prime}$ is H or lower alkyl,
  Z' is an enzyme,
  t' is an integer from 1 to 6 and v' is an integer from 2 to 6,
  n' is an integer between 1 and the molecular weight of said enzyme divided by 500; and
(b) examining said medium for the presence of a complex comprising said amphetamine and said antibody for amphetamine and/or a complex of said methamphetamine and said antibody for methamphetamine, the presence thereof indicating the presence of said amphetamine and/or methamphetamine in said sample.

48. A method according to claim 47 wherein said examining comprises measuring signal from said enzyme, the amount thereof being related to the presence of said amphetamine and/or methamphetamine in said sample.

49. A method according to claim 48 wherein said method is a homogeneous method and said medium is examined for the amount of said signal.

50. A method according to claim 48 wherein said method is a heterogeneous method and said complex, if present, is separated from said medium and said medium or said complex is examined for the amount of said signal.

51. A method according to claim 47 wherein said enzyme is glucose-6-phosphate dehydrogenase.

52. A method for determining amphetamine and/or methamphetamine in a sample suspected of containing amphetamine and/or methamphetamine, said method comprising:
(a) providing in combination in a medium:
  (i) said sample,
  (ii) a conjugate of an enzyme and an amphetamine analog and/or a conjugate of an enzyme and a methamphetamine analog,
  (iii) an antibody for amphetamine, said antibody being raised against a compound of the formula:

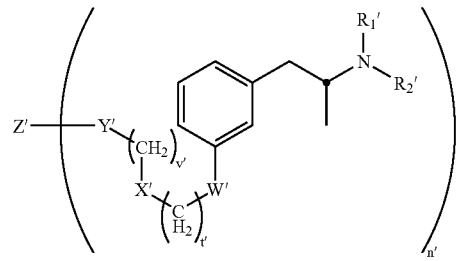

wherein:
  $R^{1\prime}$ is H and $R^{2\prime}$ is H,
  W' is O, S, or $NR^{3\prime}$ wherein $R^{3\prime}$ is H or lower alkyl,
  X' is C(O) or $SO_2$,
  Y' is bond, S or —$NR^{3\prime}$ wherein $R^{3\prime}$ is H or lower alkyl,
  Z' is a protein immunogenic carrier or a non-poly(amino acid) immunogenic carrier,
  t' is an integer from 1 to 6 and v' is an integer from 2 to 6,
  n' is an integer between 1 and the molecular weight of said antigen or said immunogenic carrier divided by 500; and/or
  (iv) an antibody for methamphetamine, said antibody being raised against a compound of the formula:

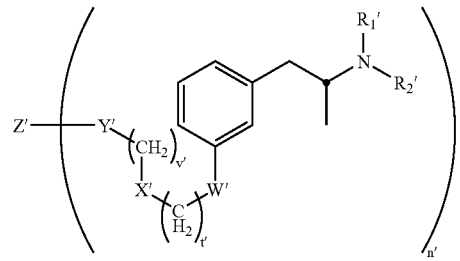

wherein:
  $R^{1\prime}$ is H and $R^{2\prime}$ is methyl,
  W' is O, S, or $NR^{3\prime}$ wherein $R^{3\prime}$ is H or lower alkyl,
  X' is C(O) or $SO_2$,
  Y' is bond, S or —$NR^{3\prime}$ wherein $R^{3\prime}$ is H or lower alkyl,
  Z' is a protein immunogenic carrier or a non-poly(amino acid) immunogenic carrier,
  t' is an integer from 1 to 6 and v' is an integer from 2 to 6, n' is an integer between 1 and the molecular weight of said antigen or said immunogenic carrier divided by 500; and (b) examining said medium for the presence of a complex comprising said amphetamine and said antibody for amphetamine and/or a complex of said methamphetamine and said antibody for methamphetamine, the presence thereof indicating the presence of said amphetamine and/or methamphetamine in said sample.

53. A method according to claim 52 wherein said examining comprises measuring signal from said enzyme, the amount thereof being related to the presence of said amphetamine and/or methamphetamine in said sample.

54. A method according to claim 53 wherein said method is a homogeneous method and said medium is examined for the amount of said signal.

55. A method according to claim 53 wherein said method is a heterogeneous method and said complex, if present, is separated from said medium and said medium or said complex is examined for the amount of said signal.

56. A method according to claim 52 wherein said enzyme is glucose-6-phosphate dehydrogenase.

57. A kit comprising in packaged combination:
  (i) an antibody for amphetamine,
  (ii) an antibody for methamphetamine,
  (iii) a compound of the formula:

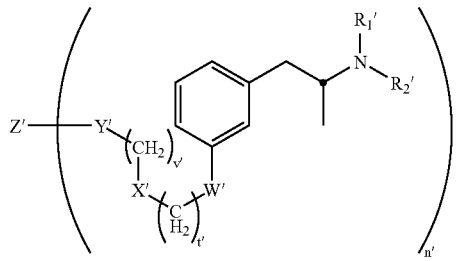

wherein:
  $R^{1'}$ is H, lower alkyl, a protecting group,
  $R^{2'}$ is H, lower alkyl, a protecting group,
  W' is O, S, or $NR^{3'}$ wherein $R^{3'}$ is H or lower alkyl,
  X' is C(O) or $SO_2$,
  Y' is bond, S or —$NR^{3'}$ wherein $R^{3'}$ is H or lower alkyl,
  Z' is an enzyme,
  t' is an integer from 1 to 6 and v' is an integer from 2 to 6,
  n' is an integer between 1 and the molecular weight of said enzyme divided by 500.

58. A kit according to claim 57 wherein said enzyme is glucose-6-phosphate dehydrogenase.

59. A kit comprising in packaged combination:
  (i) a conjugate of an enzyme and an amphetamine analog and/or a conjugate of an enzyme and a methamphetamine analog,
  (ii) an antibody for amphetamine, said antibody being raised against a compound of the formula:

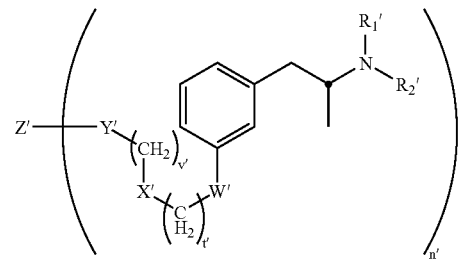

wherein:
  $R^{1'}$ is H and $R^{2'}$ is H,
  W' is O, S, or $NR^{3'}$ wherein $R^{3'}$ is H or lower alkyl,
  X' is C(O) or $SO_2$,
  Y' is bond, S or —$NR^{3'}$ wherein $R^{3'}$ is H or lower alkyl,
  Z' is a protein immunogenic carrier or a non-poly(amino acid) immunogenic carrier,
  t' is an integer from 1 to 6 and v' is an integer from 2 to 6,
  n' is an integer between 1 and the molecular weight of said antigen or said immunogenic carrier divided by 500; and/or
  (iii) an antibody for methamphetamine, said antibody being raised against a compound of the formula:

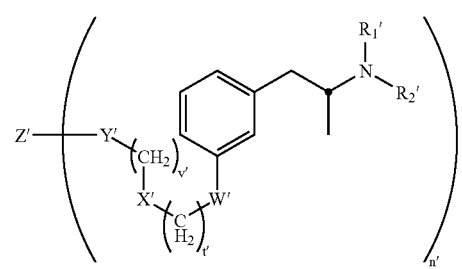

wherein:
  $R^{1'}$ is H and $R^{2'}$ is methyl,
  W" is O, S, or $NR^{3'}$ wherein $R^{3'}$ is H or lower alkyl,
  X' is C(O) or $SO_2$,
  Y' is bond, S or —$NR^{3'}$ wherein $R^{3'}$ is H or lower alkyl,
  Z' is a protein immunogenic carrier or a non-poly(amino acid) immunogenic carrier,
  t' is an integer from 1 to 6 and v' is an integer from 2 to 6,
  n' is an integer between 1 and the molecular weight of said antigen or said immunogenic carrier divided by 500.

* * * * *